US011857411B2

(12) United States Patent
Levi

(10) Patent No.: US 11,857,411 B2
(45) Date of Patent: *Jan. 2, 2024

(54) PERICARDIAL SEALING MEMBER FOR PROSTHETIC HEART VALVE

(71) Applicant: Edwards Lifesciences Corporation, Irvine, CA (US)

(72) Inventor: Tamir S. Levi, Zikhron Yaakov (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,579

(22) Filed: Oct. 25, 2022

(65) Prior Publication Data
US 2023/0063795 A1  Mar. 2, 2023

Related U.S. Application Data

(60) Continuation of application No. 17/229,143, filed on Apr. 13, 2021, which is a division of application No. (Continued)

(51) Int. Cl.
A61F 2/24 (2006.01)
A61L 27/56 (2006.01)
(Continued)

(52) U.S. Cl.
CPC .......... A61F 2/2409 (2013.01); A61F 2/2415 (2013.01); A61F 2/2418 (2013.01);
(Continued)

(58) Field of Classification Search
CPC ..... A61F 2/2418; A61F 2/2409; A61F 2/2412
See application file for complete search history.

(56) References Cited

U.S. PATENT DOCUMENTS 30,912 A    12/1860  Hancock
3,409,013 A  11/1968  Berry
(Continued)

FOREIGN PATENT DOCUMENTS

DE  0144167 C   9/1903
DE  2246526 A1  3/1973
(Continued)

OTHER PUBLICATIONS

Saporito, et al. "Bovine pericardium retail preserved in glutaraldehyde and used as a vascular patch." BMC Surg 11, 37. 2011. https://doi.org/10.1186/1471-2482-11-37.
(Continued)

Primary Examiner — Brian A Dukert
(74) Attorney, Agent, or Firm — Edwards Lifesciences; Rebecca Schewe-Mott

(57) ABSTRACT

In one embodiment, an implantable prosthetic valve can comprise an annular frame comprising an inflow end and an outflow end and being radially collapsible and expandable between a radially collapsed configuration and a radially expanded configuration, and a leaflet structure positioned within the frame and secured thereto. The prosthetic valve can further comprise an outer skirt positioned around an outer surface of the frame, the outer skirt comprising pericardial tissue having a fibrous parietal layer defining a first surface of the outer skirt and a serous parietal layer defining a second surface of the outer skirt, the pericardial tissue having been fixed by cross-linking.

20 Claims, 17 Drawing Sheets

Related U.S. Application Data

16/103,183, filed on Aug. 14, 2018, now Pat. No. 10,973,628.

(60) Provisional application No. 62/547,401, filed on Aug. 18, 2017.

(51) Int. Cl.
  *A61L 27/36* (2006.01)
  *A61L 27/50* (2006.01)
(52) U.S. Cl.
  CPC .......... *A61L 27/3625* (2013.01); *A61L 27/50* (2013.01); *A61L 27/56* (2013.01); *A61F 2/2427* (2013.01); *A61F 2230/0054* (2013.01); *A61F 2240/001* (2013.01); *A61F 2250/0063* (2013.01); *A61F 2250/0069* (2013.01); *A61L 2430/20* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,477,930 A | 10/1984 | Totten et al. |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |

(56) References Cited

U.S. PATENT DOCUMENTS

| | | |
|---|---|---|
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eldenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,422,603 B2 | 9/2008 | Lane |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,914,569 B2 * | 3/2011 | Nguyen ............... A61F 2/2418 623/2.12 |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eldenschink et al. |
| 8,348,998 B2 | 1/2013 | Pintor et al. |
| 8,403,983 B2 | 3/2013 | Quadri et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,672,999 B2 | 3/2014 | Cali et al. |
| 8,747,463 B2 | 6/2014 | Fogarty et al. |
| 9,078,781 B2 | 7/2015 | Ryan et al. |
| 9,132,007 B2 | 9/2015 | Menk et al. |
| 9,295,552 B2 | 3/2016 | McLean et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075724 A1 | 4/2005 | Svanidze et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0004299 A1 | 1/2011 | Essinger et al. |
| 2011/0015729 A1 | 1/2011 | Jimenez et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0295363 A1 * | 12/2011 | Girard ................... A61F 2/2412 623/1.26 |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |

(56) References Cited

U.S. PATENT DOCUMENTS

| | | |
|---|---|---|
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0142103 A1 | 5/2015 | Vidlund |
| 2015/0157455 A1 | 6/2015 | Hoang et al. |
| 2015/0320556 A1 | 11/2015 | Levi et al. |
| 2017/0014229 A1 | 1/2017 | Nguyen-Thien-Nhon et al. |
| 2017/0020663 A1 | 1/2017 | White |
| 2017/0056164 A1* | 3/2017 | Wang .................. A61F 2/2415 |
| 2017/0071731 A1 | 3/2017 | Dove et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |
| WO | 2015152980 A1 | 10/2015 |

OTHER PUBLICATIONS

Fanning, J.P., et al., "Transcatheter aortic valve implantation (TAVI): valve design and evolution." International Journal of Cardiology, 2013, vol. 168, No. 3, pp. 1822-1831, <DOI: 10.1016/j.ijcard 2013.07.117>.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Bailey, S. "Percutaneous Expandable Prosthetic Valves," Textbook of Interventional Cardiology vol. 2, 2nd Ed. pp. 1268-1276. 1994.

Gauvin, R. et al., "A Comparative study of bovine and porcine pericardium to highlight their potential advantages to manufacture percutaneous cardiovascular implants.", Journal of biomaterials applications, 2013, vol. 28, No. 4, pp. 552-565, <DOI: 10.1177/0885328212465482>.

H.R. Andersen "History of Percutaneous Aortic Valve Prosthesis," Herz No. 34. pp. 343-346. 2009.

H.R. Andersen, et al. "Transluminal Implantation of Artificial Heart Valve. Description of a New Expandable Aortic Valve and Initial Results with implantation by Catheter Technique in Closed Chest Pig." European Heart Journal, No. 13. pp. 704-708. 1992.

International Search for Report for International Patent Application No. PCT/US2018/046891, completed Dec. 6, 2018.

Li et al., "The organizational structure of the pericardium" Journal of Biomedical Engineering 1985; 2 (3): 149-156 Journal of Biomedical Engineering, Chengdu University of Science and Technology.

Pavonik, et al. "Development and initial Experimental Evaluation of a Prosthetic Aortic Valve for Transcatheter Placement," Cardiovascular Radiology, vol. 183, No. 1. pp. 151-154. 1992.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Uchida, "Modifications of Gianturco Expandable Wire Stents," American Journal of Roentgenology, vol. 150. pp. 1185-1187. 1986.

Wheatley, "Valve Prostheses," Operative Surgery, 4th ed. pp. 415-424. 1986.

\* cited by examiner

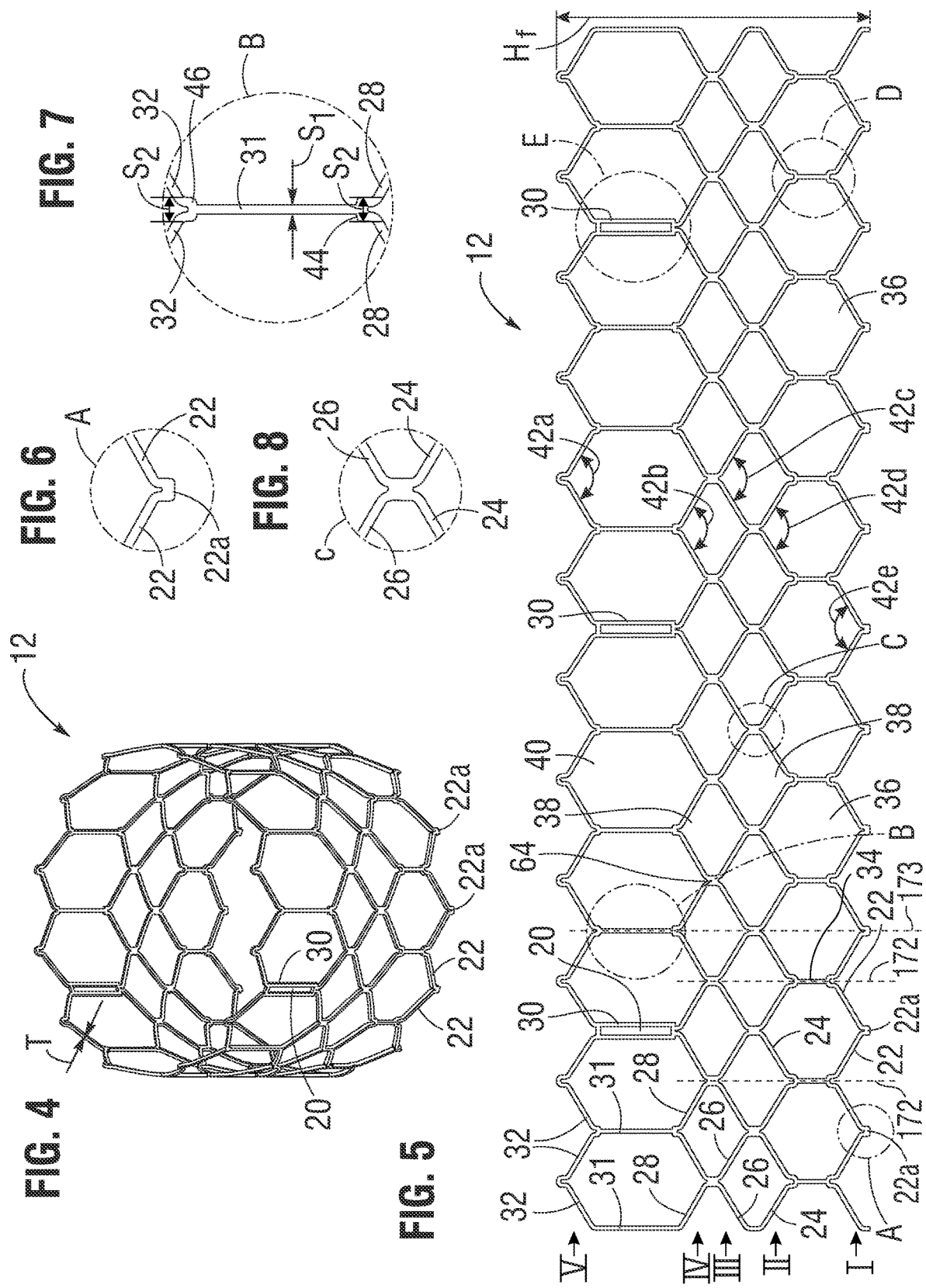

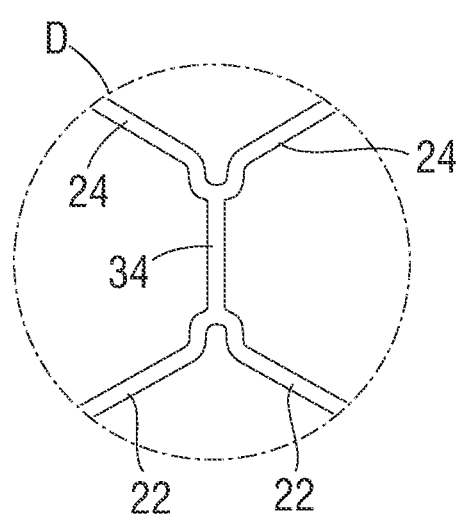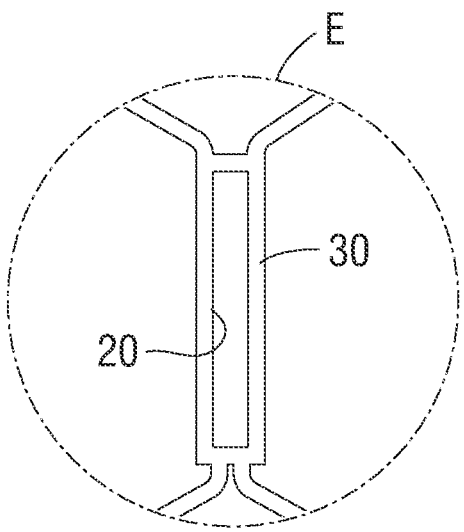

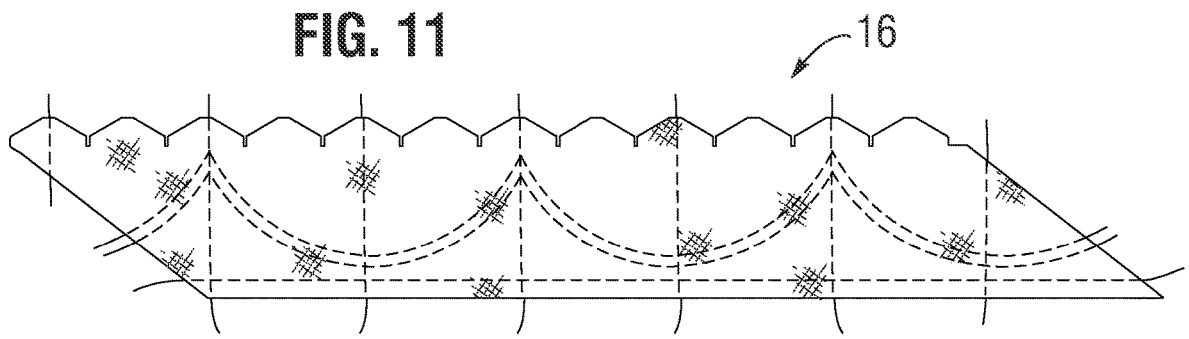
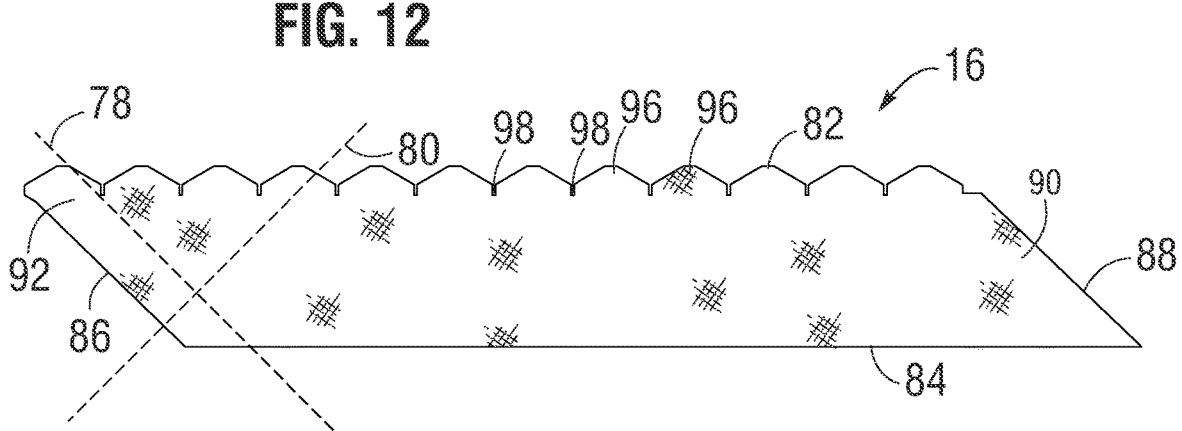
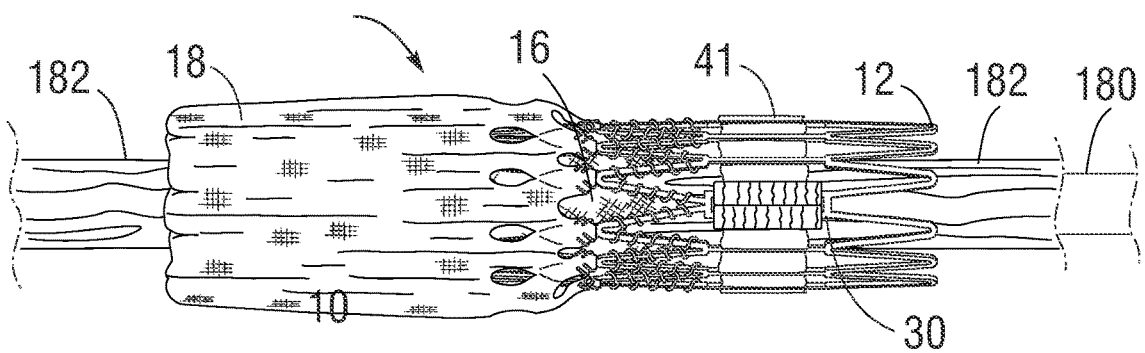

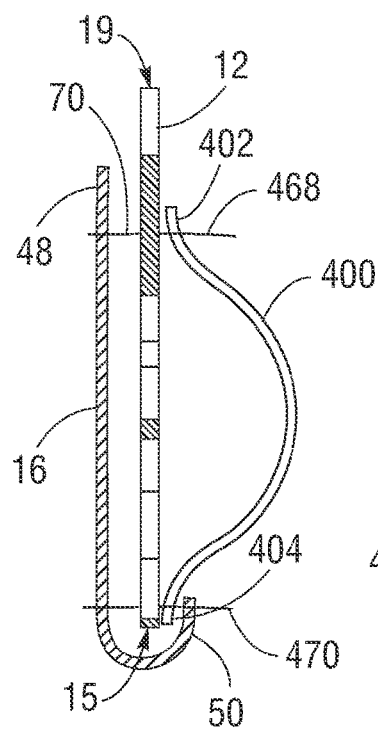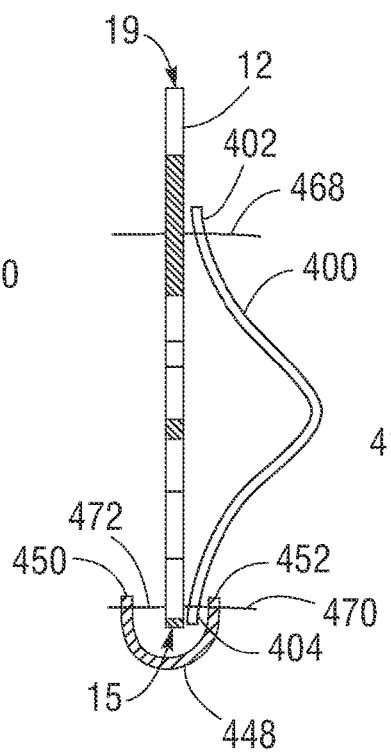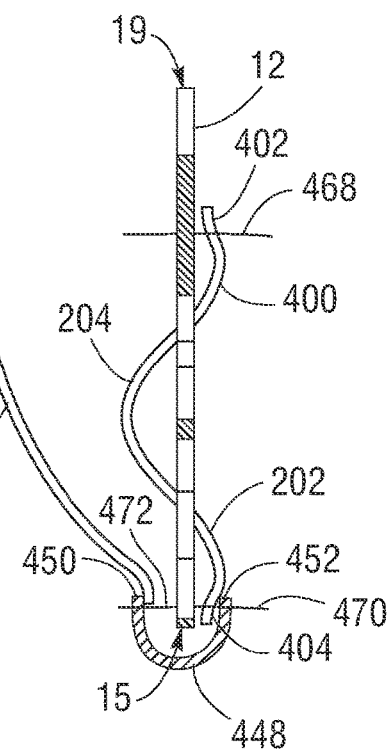

PERICARDIAL SEALING MEMBER FOR PROSTHETIC HEART VALVE

CROSS REFERENCE TO RELATED APPLICATIONS

This application is a continuation of U.S. application Ser. No. 17/229,143, filed Apr. 13, 2021, which is a divisional of U.S. application Ser. No. 16/103,183, filed Aug. 14, 2018, now U.S. Pat. No. 10,973,628, which claims the benefit of U.S. Provisional Application No. 62/547,401, filed Aug. 18, 2017, each of which applications are incorporated by reference herein.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled, and which can be percutaneously introduced in a collapsed configuration on a catheter and expanded in the desired position by balloon inflation or by utilization of a self-expanding frame or stent. A challenge in catheter-implanted prosthetic valves is control of perivalvular leakage around the valve, which can occur for a period of time following initial implantation. An additional challenge includes the process of crimping such a prosthetic valve to a profile suitable for percutaneous delivery to a subject.

SUMMARY

The foregoing and other objects, features, and advantages of the disclosure will become more apparent from the following detailed description, which proceeds with reference to the accompanying figures.

In one embodiment, an implantable prosthetic valve can comprise an annular frame, a leaflet structure positioned within the frame, and an outer skirt positioned around an outer surface of the frame. The annular frame can comprise an inflow end and an outflow end and can be radially collapsible and expandable between a radially collapsed configuration and a radially expanded configuration. The outer skirt can comprise pericardial tissue having a fibrous parietal layer defining a first surface of the outer skirt and a serous parietal layer defining a second surface of the outer skirt. The outer skirt can be positioned such that the first surface is facing away from the frame and the second surface is facing towards the frame.

In some embodiments, the outer skirt can comprise bovine pericardial tissue.

In some embodiments, the outer skirt can be laser milled to reduce its thickness.

In some embodiments, the thickness of the outer skirt can be between 50 µm and 150 µm.

In some embodiments, the outer skirt can comprise a plurality of openings or slits.

In some embodiments, at least one of the openings or slits can be elongated in an axial direction.

In some embodiments, the outer skirt can comprise an outflow edge portion and an inflow edge portion. The outflow edge portion can comprise a plurality of alternating projections and notches and the projections can be secured to the frame and the notches can be not directly secured to the frame.

In some embodiments, the prosthetic valve can further comprise a reinforcing strip that wraps around the inflow end of the frame such that a first end portion of the reinforcing strip extends at least partially along an inner surface of the frame and is secured thereto, and a second end portion of the reinforcing strip extends at least partially along an outer surface of the outer skirt and is secured thereto.

In some embodiments, the outer skirt can be secured to the frame with sutures.

In some embodiments, the prosthetic valve can further comprise an inner skirt positioned around an inner surface of the frame and secured thereto.

In some embodiments, the inner skirt can comprise an outflow edge portion secured to the frame and an inflow edge portion that wraps around the inflow end of the frame and the inflow end of the outer skirt. In such embodiments, the inflow end portion can extend at least partially along an outer surface of the outer skirt and can be secured thereto.

In some embodiments, the prosthetic valve can further comprise one or more strips positioned around an outer surface of the outer skirt and secured thereto.

In some embodiments, the strips can comprise a fabric material.

In another embodiment, a method of manufacturing a prosthetic heart valve can comprise providing a piece of pericardial tissue comprising a fibrous parietal layer and a serous parietal layer, reducing the thickness of the piece of pericardial tissue by removing a portion of the serous parietal layer, and positioning the pericardial tissue around an outer surface of a frame of the prosthetic heart valve and securing it thereto. The fibrous parietal layer can define a first surface of the tissue and the serous parietal layer can define a second surface of the tissue. The pericardial tissue can be positioned around the frame such that the first surface is facing away from the frame and the second surface is facing towards the frame.

In some embodiments, the pericardial tissue can have a thickness between 50 µm and 100 µm.

In some embodiments, the act of reducing the thickness of the piece of pericardial tissue can comprise laser milling the serous parietal layer.

In some embodiments, the method can further comprise forming slits or openings in the piece of pericardial tissue before positioning it on the frame.

In some embodiments, the method can further comprise connecting a plurality of prosthetic leaflets to the inside of the frame.

In another embodiment a method of implanting a prosthetic heart valve can comprise inserting a distal end portion of a delivery apparatus and a prosthetic heart valve coupled to the distal end portion of the delivery apparatus into a patient's body, positioning the prosthetic heart valve adjacent a native valve of the patient's heart, and radially expanding the prosthetic heart valve. The prosthetic heart valve can comprise an annular frame, a leaflet structure positioned within the frame and secured thereto, and an outer skirt positioned around an outer surface of the frame. The annular frame can comprise an inflow end and an outflow end and can be radially collapsible and expandable between a radially collapsed configuration and a radially expanded configuration. The outer skirt can comprise pericardial tissue having a fibrous parietal layer defining an outer surface of the skirt and a serous parietal layer defining an inner surface of the skirt. The prosthetic heart valve can be expanded such that the fibrous parietal layer can contact the surrounding native tissue.

In some embodiments, the outer skirt can comprise a plurality of slits or openings such that antegrade blood can flow through the slits or openings.

BRIEF DESCRIPTION OF THE DRAWINGS

FIGS. 4-10 show an exemplary frame of the prosthetic heart valve of FIG. 1.

FIGS. 11-12 show an exemplary inner skirt of the prosthetic heart valve of FIG. 1.

FIG. 13 shows the prosthetic heart valve of FIG. 1 in a collapsed configuration and mounted on an exemplary balloon catheter.

FIGS. 27-29 show various cross-sectional views of an exemplary embodiment of a prosthetic heart valve.

DETAILED DESCRIPTION

Figure 1:
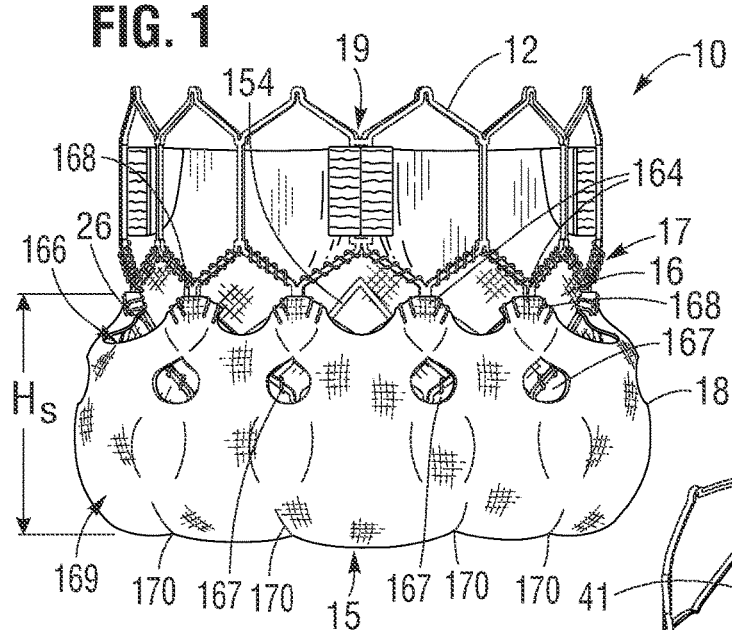
FIGS. 1-3 show an exemplary embodiment of a prosthetic heart valve.
Figure 2:
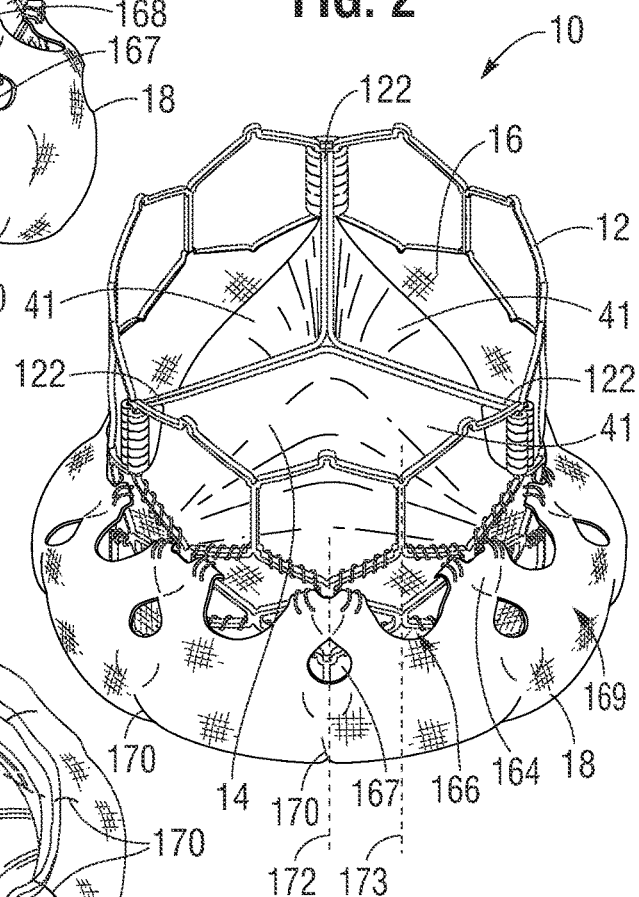
Figure 3:
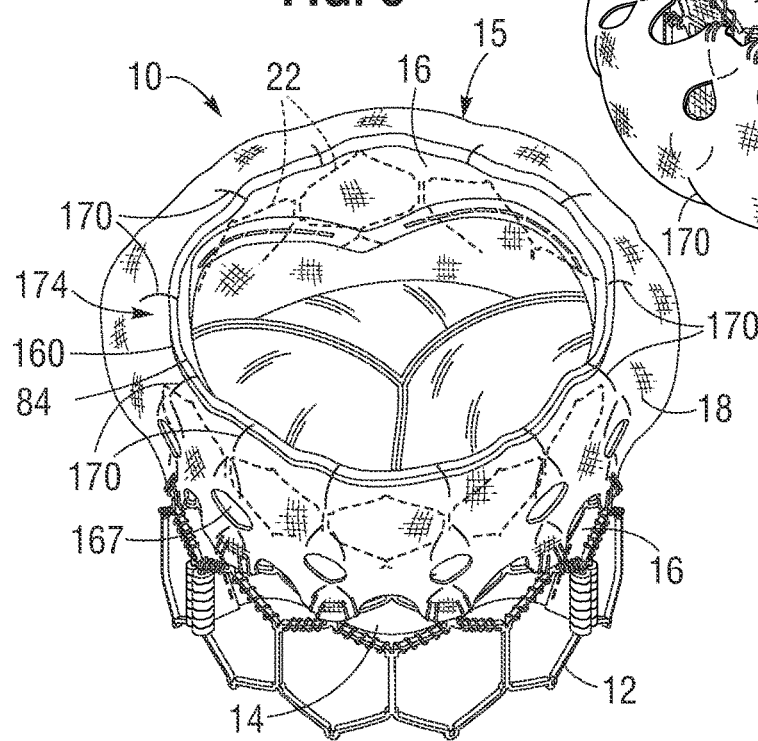

FIGS. 1-3 show various views of a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular sealing means or sealing member. The prosthetic valve 10 can have an inflow end portion 15, an intermediate portion 17, and an outflow end portion 19. In the illustrated embodiment, the perivalvular sealing means comprises an outer skirt 18 (which can also be referred to as an outer sealing member).

The valvular structure 14 can comprise three leaflets 41, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 21 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 41 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference in its entirety herein.

The bare frame 12 is shown in FIG. 4. The frame 12 can be formed with a plurality of circumferentially spaced slots, or commissure windows, 20 (three in the illustrated embodiment) that are adapted to connect the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol). When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. When MP35N® alloy is used as the frame material, as compared to stainless steel, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 5.

Each commissure window frame portion 30 connects to a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

As best shown in FIG. 7, the lower end of the strut 31 is connected to two struts 28 at a node or junction 44, and the upper end of the strut 31 is connected to two struts 32 at a node or junction 46. The strut 31 can have a thickness 51 that is less than the thicknesses S2 of the junctions 44, 46. The junctions 44, 46, along with junctions 64, prevent full closure of openings 40. FIG. 13 shows the prosthetic valve 10 crimped on a balloon catheter. As can be seen, the geometry of the struts 31, and junctions 44, 46, and 64 assists in creating enough space in openings 40 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

In addition, the inflow and outflow ends of a frame generally tend to over-expand more so than the middle portion of the frame due to the "dog-boning" effect of the balloon used to expand the prosthetic valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In one type of prosthetic valve construction, portions of the leaflets protrude longitudinally beyond the outflow end of the frame when the prosthetic valve is crimped if the leaflets are connected too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of connecting the leaflets at a location spaced away from the outflow end of the frame is that when the prosthetic valve is crimped on a delivery catheter, the outflow end of the frame 12 rather than the leaflets 41 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 41, so as to avoid damage to the leaflets.

Also, as can be seen in FIG. 5, the openings 36 of the lowermost row of openings in the frame are relatively larger than the openings 38 of the two intermediate rows of openings. This allows the frame, when crimped, to assume an overall tapered shape that tapers from a maximum diameter at the outflow end of the prosthetic valve to a minimum diameter at the inflow end of the prosthetic valve.

When crimped, the frame 12 can have a reduced diameter region extending along a portion of the frame adjacent the inflow end of the frame that generally corresponds to the region of the frame covered by the outer skirt 18. In some embodiments, the reduced diameter region is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a first diameter of 14 French at the outflow end of the prosthetic valve and a second diameter of 12 French at the inflow end of the prosthetic valve.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at least one of its edges than at its center. In one implementation, the skirt 16 can comprise a PET skirt having a thickness of about 0.07 mm at its edges and about 0.06 mm at its center. The thinner skirt can provide for better crimping performances while still providing good sealing.

Figure 20:
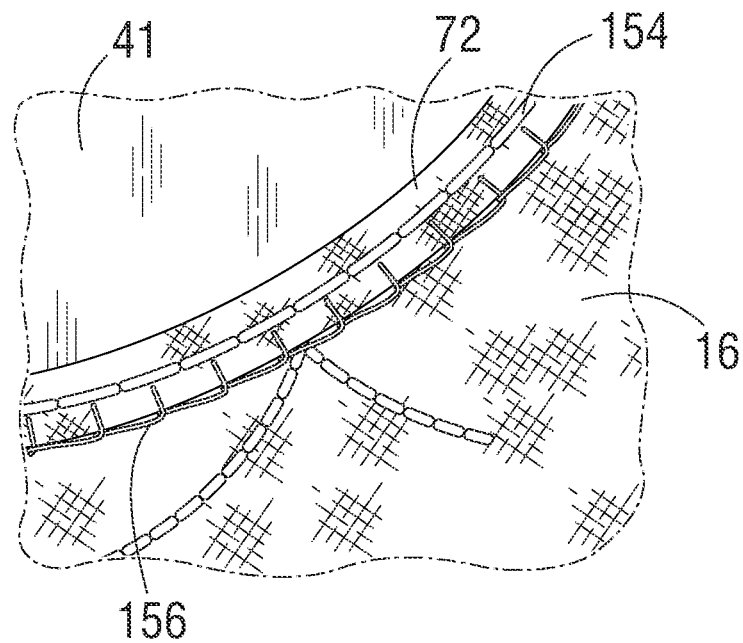
FIGS. 20-21 show the assembly of the leaflet structure with the inner skirt along a lower edge of the leaflets.
Figure 21:
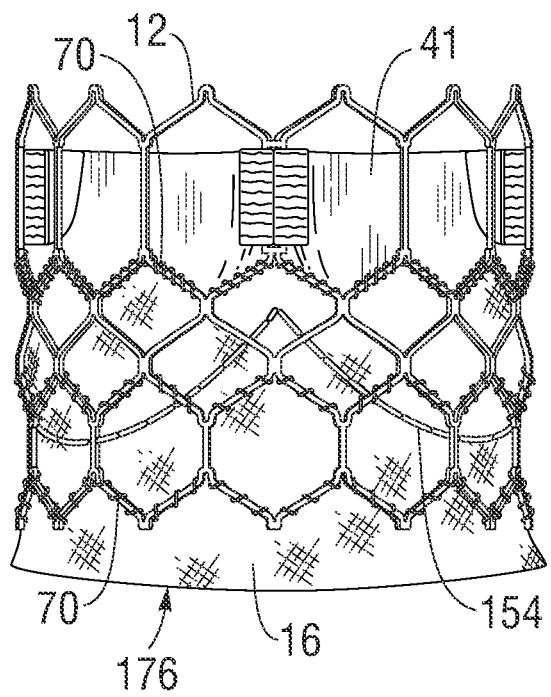

The skirt 16 can be secured to the inside of frame 12 via sutures 70, as shown in FIG. 21. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 20. Sutures 154, which secure the PET strip and the leaflet structure 14 to skirt 16, can be any suitable suture, such as Ethibond Excel® PET suture (Johnson & Johnson, New Brunswick, New Jersey). Sutures 154 desirably track the curvature of the bottom edge of leaflet structure 14, as described in more detail below.

Some fabric skirts comprise a weave of warp and weft fibers that extend perpendicularly to each other and with one set of the fibers extending longitudinally between the upper and lower edges of the skirt. When the metal frame to which such a fabric skirt is secured is radially compressed, the overall axial length of the frame increases. However, a fabric skirt with limited elasticity cannot elongate along with the frame and therefore tends to deform the struts of the frame and to prevent uniform crimping.

Referring to FIG. 12, in one embodiment, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees (e.g., 15-75 degrees or 30-60 degrees) relative to the upper and lower edges 82, 84. For example, the skirt 16 can be formed by weaving the fibers at 45 degree angles relative to the upper and lower edges of the fabric. Alternatively, the skirt 16 can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 12, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt can be that of a rhomboid or parallelogram.

Figure 14:
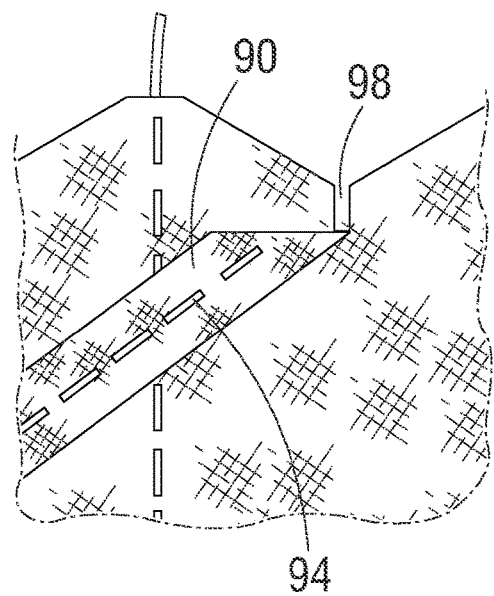
FIGS. 14-16 show the assembly of the inner skirt of FIG. 11 with the frame of FIG. 4.
Figure 15:
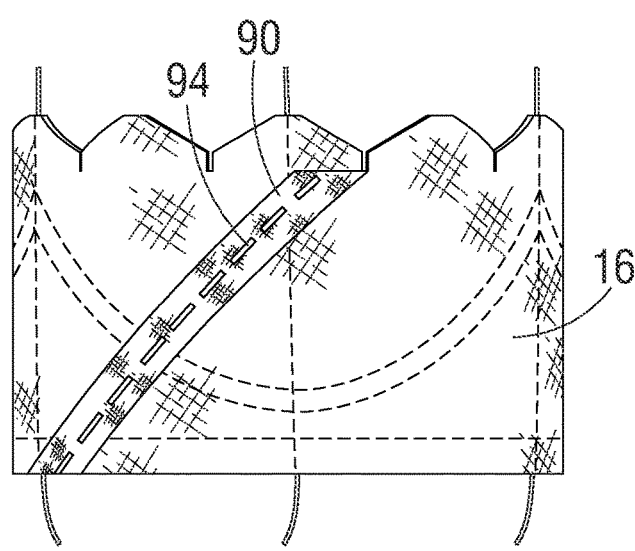
Figure 16:
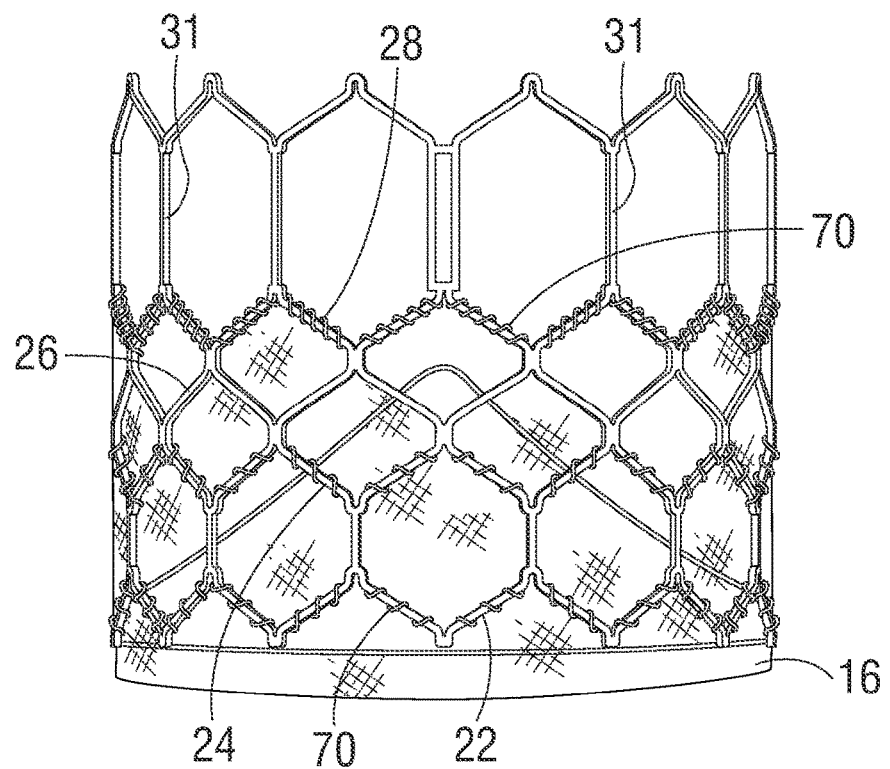

FIGS. 14 and 15 show the inner skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the inner skirt 16 can be formed with a plurality of projections 96 that define an undulating shape that generally follows the shape or contour of the fourth row of struts 28 immediately adjacent the lower ends of axial struts 31. In this manner, as best shown in FIG. 16, the upper edge of the inner skirt 16 can be tightly secured to struts 28 with sutures 70. The inner skirt 16 can also be formed with slits 98 to facilitate attachment of the skirt to the frame. Slits 98 can be dimensioned so as to allow an upper edge portion of the inner skirt 16 to be partially wrapped around struts 28 and to reduce stresses in the skirt during the attachment procedure. For example, in the illustrated embodiment, the inner skirt 16 is placed on the inside of frame 12 and an upper edge portion of the skirt is wrapped around the upper surfaces of struts 28 and secured in place with sutures 70. Wrapping the upper edge portion of the inner skirt 16 around struts 28 in this manner provides for a stronger and more durable attachment of the skirt to the frame. The inner skirt 16 can also be secured to the first, second, and/or third rows of struts 22, 24, and 26, respectively, with sutures 70.

Referring again to FIG. 12, due to the angled orientation of the fibers relative to the upper and lower edges in this embodiment, the skirt can undergo greater elongation in the axial direction (i.e., in a direction from the upper edge 82 to the lower edge 84).

Thus, when the metal frame 12 is crimped (as shown in FIG. 13), the inner skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 16 formed from 20-denier yarn, the yarn density can be about 15% to about 30% lower than in a typical PET skirt. In some examples, the yarn spacing of the inner skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to facilitate uniform crimping to the smallest possible diameter. Additionally, cutting diagonal sutures in a vertical manner may leave loose fringes along the cut edges. The oblique edges 86, 88 help minimize this from occurring.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area. This configuration can avoid stress concentrations at the suture line 154, which attaches the lower edges of the leaflets to the inner skirt 16.

As noted above, the leaflet structure 14 in the illustrated embodiment includes three flexible leaflets 41 (although a greater or a smaller number of leaflets can be used). Additional information regarding the leaflets, as well as additional information regarding skirt material, can be found, for example, in U.S. patent application Ser. No. 14/704,861, filed May 5, 2015, which is incorporated by reference in its entirety.

The leaflets 41 can be secured to one another at their adjacent sides to form commissures 122 of the leaflet structure. A plurality of flexible connectors 124 (one of which is shown in FIG. 17) can be used to interconnect pairs of adjacent sides of the leaflets and to connect the leaflets to the commissure window frame portions 30 (FIG. 5).

Figure 17:
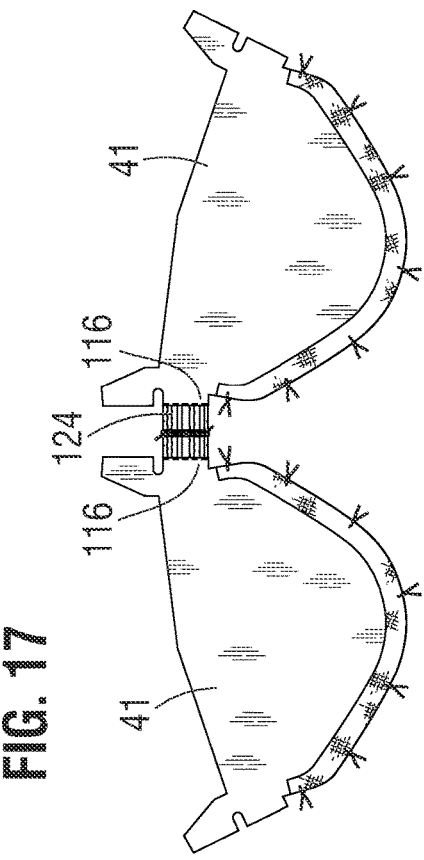
FIGS. 17-18 show the assembly of an exemplary leaflet structure.
Figure 18:
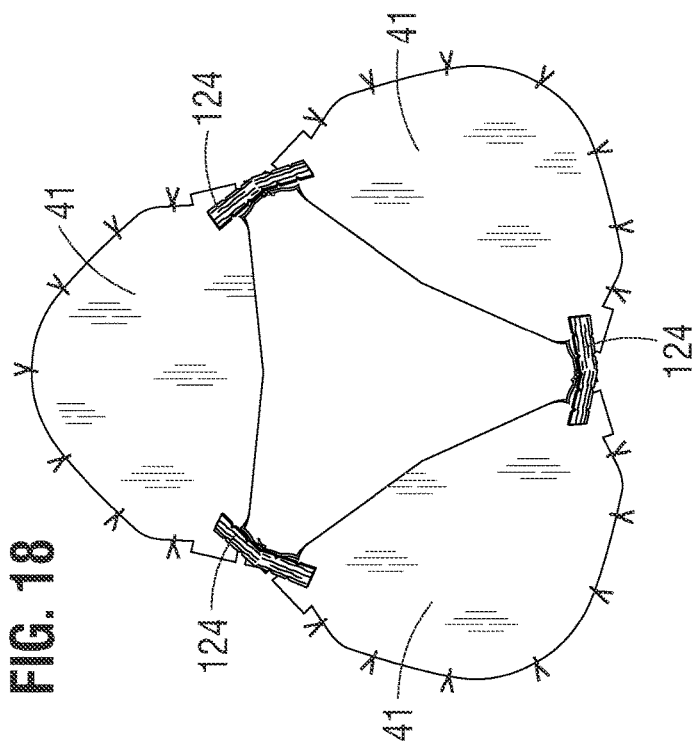

FIG. 17 shows the adjacent sides of two leaflets 41 interconnected by a flexible connector 124. Three leaflets 41 can be secured to each other side-to-side using three flexible connectors 124, as shown in FIG. 18. Additional information regarding connecting the leaflets to each other, as well as connecting the leaflets to the frame, can be found, for example, in U.S. Patent Application Publication No. 2012/0123529, which is incorporated by reference herein in its entirety.

As noted above, the inner skirt 16 can be used to assist in suturing the leaflet structure 14 to the frame. The inner skirt 16 can have an undulating temporary marking suture to guide the attachment of the lower edges of each leaflet 41. The inner skirt 16 itself can be sutured to the struts of the frame 12 using sutures 70, as noted above, before securing the leaflet structure 14 to the skirt 16. The struts that intersect the marking suture desirably are not attached to the inner skirt 16. This allows the inner skirt 16 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

Figure 19:
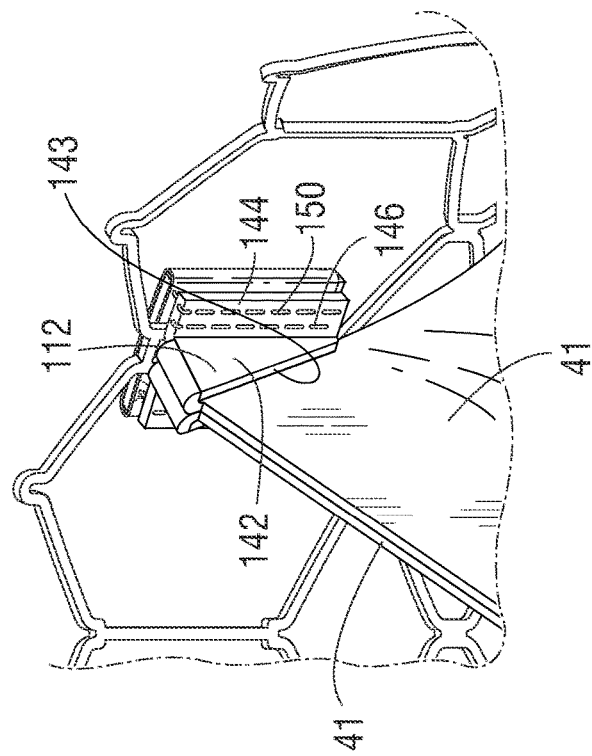
FIG. 19 shows the assembly of commissure portions of the leaflet structure with window frame portions of the frame.

FIG. 19 shows one specific approach for securing the commissure portions 122 of the leaflet structure 14 to the commissure window frame portions 30 of the frame. In this approach, the flexible connector 124 (FIG. 18) securing two adjacent sides of two leaflets is folded widthwise and the upper tab portions 112 are folded downwardly against the flexible connector. Each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, the commissure tab assembly is inserted through the commissure window 20 of a corresponding window frame portion 30, and the folds outside of the window frame portion 30 can be sutured to portions 144.

FIG. 19 also shows that the folded down upper tab portions 112 can form a double layer of leaflet material at the commissures. The inner portions 142 of the upper tab portions 112 are positioned flat against layers of the two leaflets 41 forming the commissures, such that each commissure comprises four layers of leaflet material just inside of the window frames 30. This four-layered portion of the commissures can be more resistant to bending, or articulating, than the portion of the leaflets 41 just radially inward from the relatively more-rigid four-layered portion. This causes the leaflets 41 to articulate primarily at inner edges 143 of the folded-down inner portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis adjacent to the window frame 30, with each inner portion 142 folding out against the respective outer portion 144. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame portions 30, the lower edges of the leaflets 41 between the commissure tab assemblies can be sutured to the inner skirt 16. For example, as shown in FIG. 20, each leaflet 41 can be sutured to the inner skirt 16 along suture line 154 using, for example, Ethibond Excel® PET thread. The sutures can be in-and-out sutures extending through each leaflet 41, the inner skirt 16, and each reinforcing strip 72. Each leaflet 41 and respective reinforcing strip 72 can be sewn separately to the inner skirt 16. In this manner, the lower edges of the leaflets are secured to the frame 12 via the inner skirt 16. As shown in FIG. 20, the leaflets can be further secured to the skirt with blanket sutures 156 that extend through each reinforcing strip 72, leaflet 41 and the inner skirt 16 while looping around the edges of the reinforcing strips 72 and leaflets 41. The blanket sutures 156 can be formed from PTFE suture material. FIG. 21 shows a side view of the frame 12, leaflet structure 14 and the inner skirt 16 after securing the leaflet structure 14 and the inner skirt 16 to the frame 12 and the leaflet structure 14 to the inner skirt 16.

Figure 22:
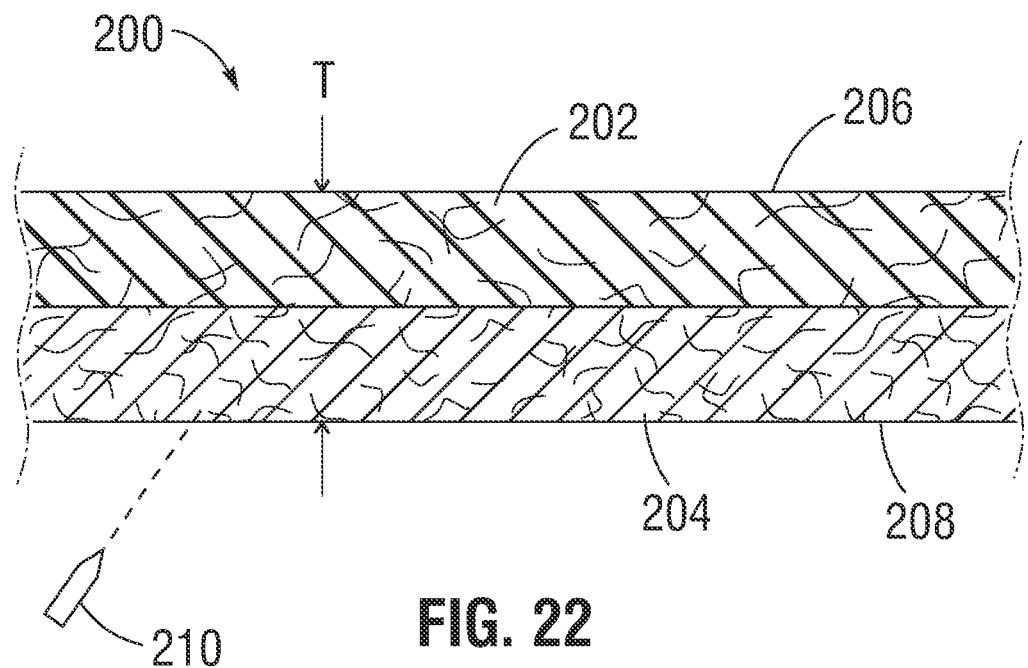
FIG. 22 shows a cross-sectional view of pericardial tissue that can be formed into an outer skirt.

FIG. 22 shows a cross-sectional view of a patch or section of pericardial tissue 200 that can be formed into an alternative embodiment of an outer skirt. The pericardial tissue 200 can be bovine pericardium, porcine pericardium, equine pericardium, kangaroo pericardium, or pericardium from other sources. The pericardial tissue 200 has a rough or fibrous layer 202 having a rough surface 206 on one side and a smooth layer 204 having a smooth surface 208 on the opposite side that is relatively smoother and less fibrous than the rough surface 206. The tissue 200 can be formed from a section of the parietal pericardial membrane comprising a fibrous parietal layer (the outermost layer of the pericardium) forming the rough layer 202 and a serous parietal layer (the outer serous layer) forming the smooth layer 204.

The tissue 200 can be harvested and prepared for use in an implant using those techniques and mechanisms known for processing pericardial tissue for heart valve leaflets. A process for preparing pericardial tissue for heart valve leaflets typically includes first obtaining a fresh pericardial sac from a source animal, and then cutting the sac open along predetermined anatomical landmarks to obtain a parietal pericardial membrane. The parietal pericardial membrane can be flattened and typically cleaned of excess fat and other impurities. After trimming obviously unusable areas, a window or patch of tissue can be fixed, typically by immersing in an aldehyde to cross-link the tissue. Rough edges of the tissue window can be removed and the tissue can be bio-sorted to result in a tissue section. The process of bio-sorting involves visually inspecting the window for unusable areas, and trimming the section therefrom. Further details regarding the process for processing pericardial tissue are disclosed in U.S. Pat. Nos. 8,846,390 and 9,358,107, which are incorporated herein by reference in their entirety.

In the illustrated example of FIG. 22, following initial processing of the pericardial tissue as described in the preceding paragraph, the overall thickness of the parietal pericardial membrane can be reduced by removing a portion of the smooth layer 204 of the pericardial tissue 200, such as by using a laser 210 in a laser milling process, until the pericardial tissue has a desired thickness T. In some embodiments, the final thickness T after milling is between 50-150 µm, and more preferably between 100-150 µm, with 100 µm being a specific example. Alternatively, the pericardial tissue 200 can be milled or otherwise formed to any other thickness T. After the tissue is processed, the pericardial tissue 200 has a smooth layer 204, a rough layer 202, a thickness T, and it can be formed into an outer skirt as discussed in connection with FIGS. 23 and 26 below.

In addition to laser tissue removal described above, various mechanical devices for skiving or shaving tissue such as razor or planing devices may be used to remove some of the tissue. For instance, a device having a flat platen over which a planing razor or blade translates may be substituted for the linear laser configuration of FIG. 22. Other physical configurations for creating relative tissue/razor movement are contemplated, such as for instance using a lathe-like razor to smooth the outer surface of the tissue. Each of these devices may be automatically or computer-controlled using an optical surface measuring component to control the depth of cut. Abrasive tissue removal (e.g., sanding or rasping) can also be used, though the grit of the tool should be relatively fine. In other embodiments, a dermatome can be used for skiving or shaving of a portion of the smooth tissue layer 204. Further details regarding the use of a dermatome for removing portions of tissue from pericardial tissue are disclosed in U.S. Pat. No. 8,846,390.

In alternative embodiments, the thickness of the pericardial tissue 200 can be reduced by removing a portion of the fibrous parietal layer using any of the techniques described above in lieu of or in addition to removing a portion of the serous parietal layer.

Figure 23:
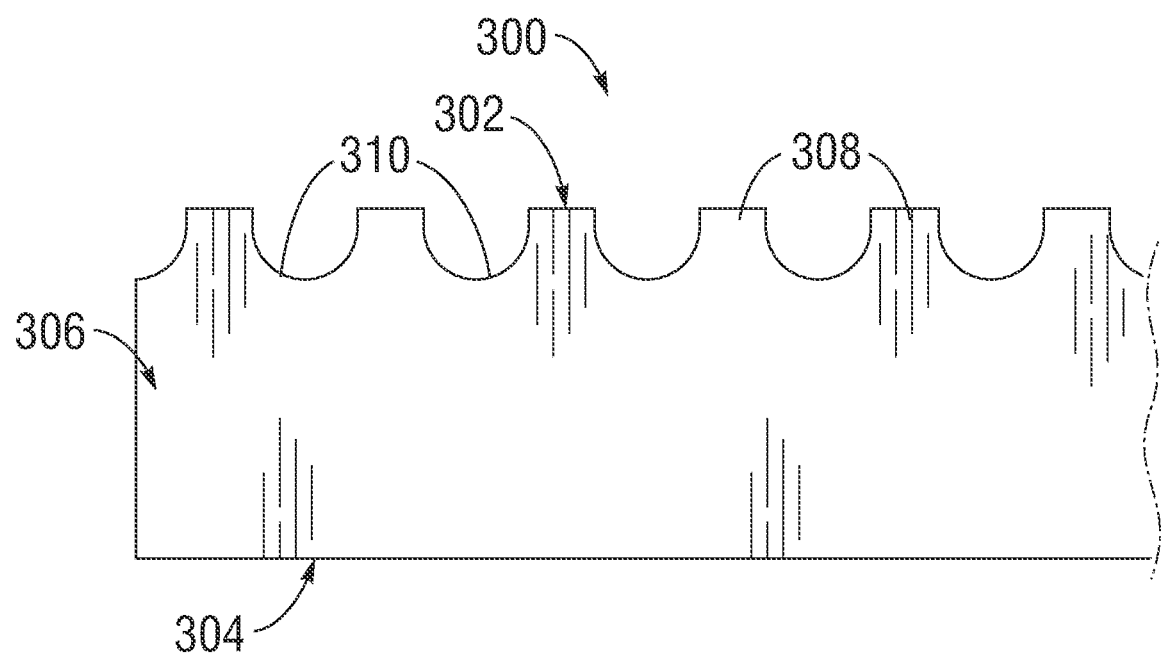
FIG. 23 shows an exemplary outer skirt formed from the pericardial tissue of FIG. 22.
Figure 24:
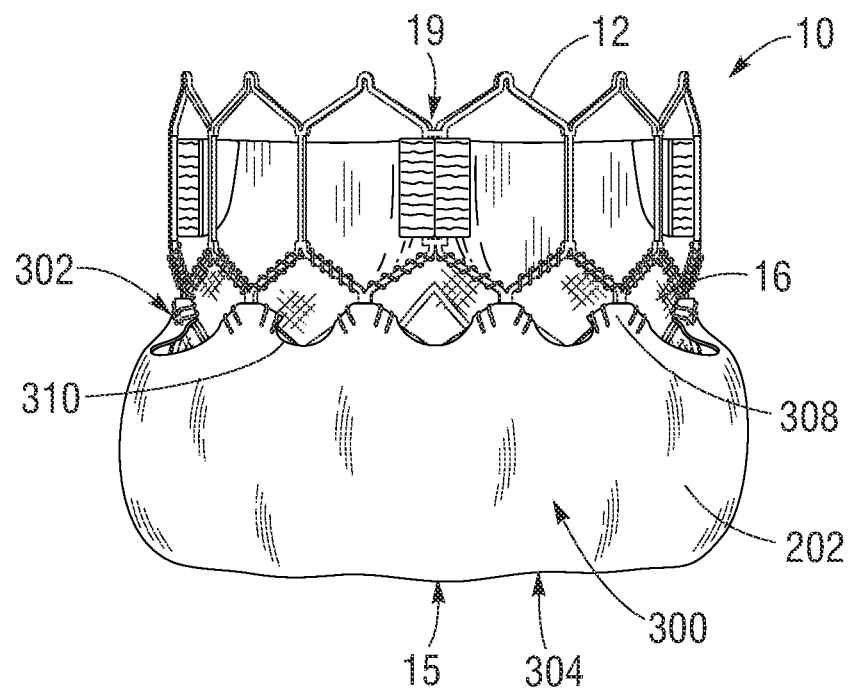
FIG. 24 shows an exemplary prosthetic heart valve using the outer skirt of FIG. 23.

FIGS. 23-24 show various views of an exemplary outer skirt 300 formed from the pericardial tissue 200 of FIG. 22. FIG. 23 shows a flattened view of the outer skirt 300 prior to its attachment to a prosthetic heart valve. FIG. 24 shows the outer skirt 300 attached to the prosthetic heart valve 10.

Referring to FIG. 23, the outer skirt 300 can comprise a first end portion 302 (i.e., the upper end portion as depicted in FIG. 23; also the outflow end portion in the illustrated embodiment), a second end portion 304 (i.e., the lower end portion as depicted in FIG. 23; also the inflow end portion in the illustrated embodiment), and an intermediate portion 306 disposed between the first and second end portions 302, 304. The first end portion 302 of the outer skirt 300 can include a plurality of alternating projections 308 and notches 310, or castellations. In other embodiments, first end portion 302 can be formed without any projections 308 or notches 310 and instead can be substantially straight.

Referring to FIG. 24, the outer skirt 300 is attached to the prosthetic heart valve 10. The projections 308 of the first end portion 302 can be attached to the inner skirt 16 and/or the frame 12 of the prosthetic heart valve 10 using sutures (as shown) and/or an adhesive. The lower end portion 304 can be attached to the inner skirt 16 and/or the frame 12 of the prosthetic heart valve 10 using sutures, adhesive, or any other suitable attachment means.

In the illustrated example of FIG. 24, the outer skirt 300 is secured to the frame 12 with the rough surface 206 of the pericardial tissue 200 facing away from the frame 12 and the smooth surface 208 facing the frame 12. As such, when the prosthetic heart valve 10 of FIG. 24 having the outer skirt 300 is implanted in a patient, the rough surface 206 of the pericardium 200 faces the native tissue of the patient. The rough surface 206 facing or being in contact with the native tissue can help disturb antegrade blood flow between the outer skirt 300 and the native anatomy of the patient, which can enhance tissue ingrowth and proliferation and help seal any gaps between the prosthetic heart valve 10 and the native anatomy to reduce and/or eliminate perivalvular leakage. In addition, if the outer skirt 300 protrudes inwardly through the frame 12 during cycling or when the prosthetic heart valve 10 is crimped in a radially collapsed configuration, any contact between the valvular structure 14 and the outer skirt 300 will be with the smooth surface 208 of the pericardium 200, which can be less abrasive than outer skirts made of PET or other fabrics and therefore the outer skirt 300 made from pericardium 200 can help protect the leaflets of the valvular structure 14. It should be noted that while outer skirt 300 is illustrated as being attached somewhat loosely, that is, with some slack in the intermediate portion 306 of the outer skirt 300, it can also be attached so as to fit more snugly against the outer surface of the frame 12.

Figure 25:
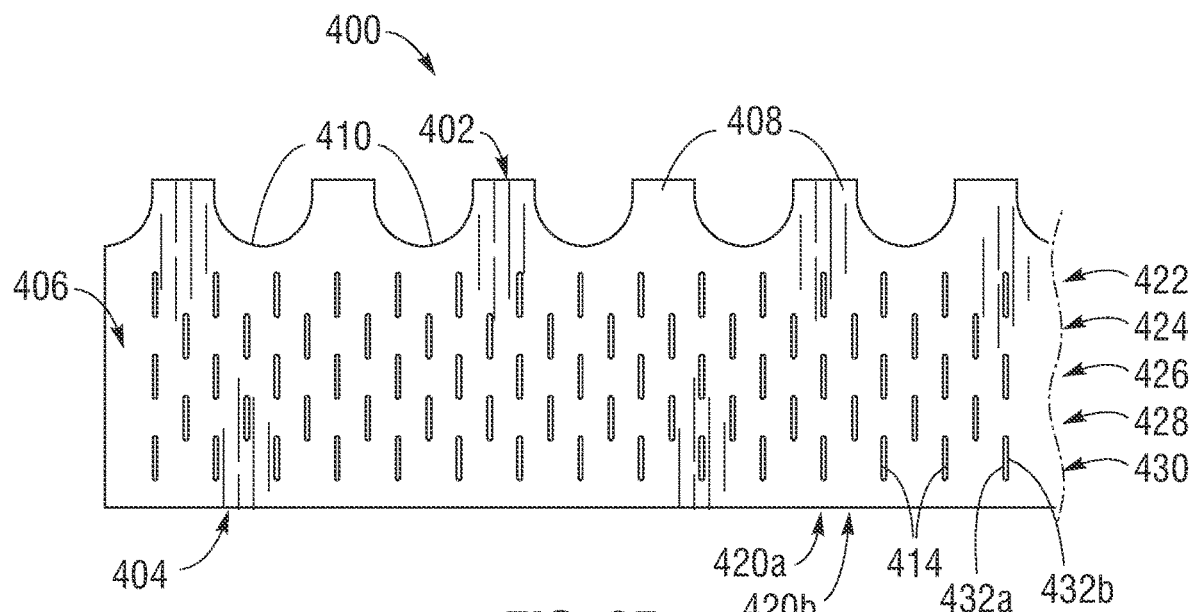
FIG. 25 shows another exemplary outer skirt formed from the pericardial tissue of FIG. 22.
Figure 26:
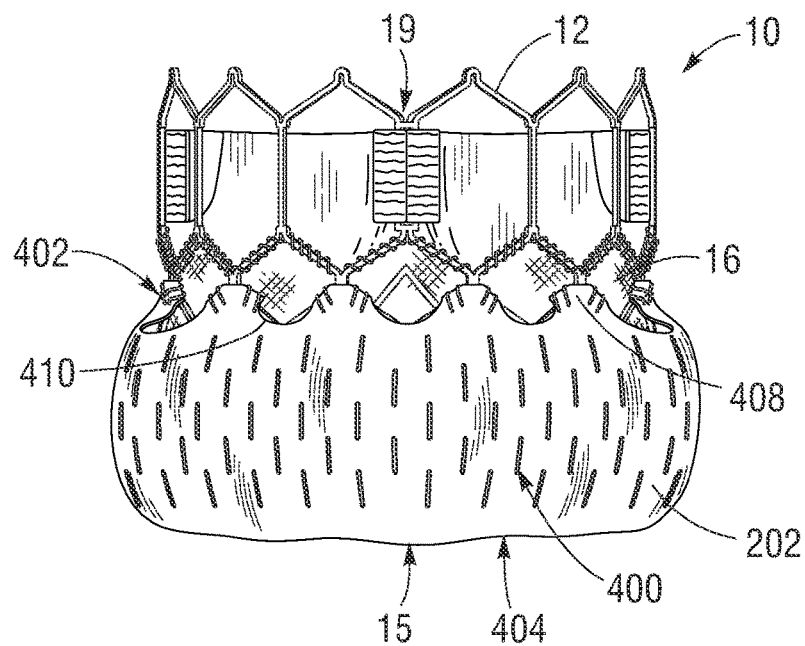
FIG. 26 shows another exemplary prosthetic heart valve using the outer skirt of FIG. 25.

FIGS. 25-26 show various views of another exemplary outer skirt 400 formed from the pericardial tissue 200 of FIG. 22. FIG. 25 shows a flattened view of the outer skirt 400 prior to its attachment to a prosthetic heart valve. FIG. 26 shows the outer skirt 400 attached to the prosthetic heart valve 10.

Referring to FIG. 25, the outer skirt 400 can comprise a first end portion 402 (i.e., the upper end portion as depicted in FIG. 25), a second end portion 404 (i.e., the lower end portion as depicted in FIG. 25), and an intermediate portion 406 disposed between the first and second end portions 402, 404. The first end portion 402 of the outer skirt 400 can include a plurality of alternating projections 408 and notches 410, or castellations. As noted previously, in other embodiments, first end portion 402 can be formed without any projections 408 or notches 410 and instead can be substantially straight The intermediate portion 406 can comprise a plurality of slits or openings 414. The slits 414 can be cut or otherwise formed in a longitudinal direction (i.e., an axial direction when the outer skirt 400 is attached to the frame of a prosthetic heart valve). The slits 414 can be laser cut or formed by any other means. In the illustrated embodiment of FIG. 25, the slits 414 are elongated axially and are arranged in five rows 422, 424, 426, 428, and 430. In other embodiments, the slits 414 can be arranged in more or less than five rows. In the illustrated embodiment of FIG. 25, the rows 422, 426, and 430 of slits 414 are circumferentially aligned with each other and are offset from rows 424 and 428 of slits 414, which are circumferentially aligned with each other.

In some embodiments, each slit 414 includes first and second opposing longitudinal sides 432a, 432b, respectively, that are spaced apart from each other to define a permanent open gap therebetween. In other embodiments, the longitudinal sides 432a, 432b of a slit 414 are in contact with each other (and do not define a permanent open gap therebetween) in the absence of hemodynamic forces, but can move away from each other under hemodynamic forces to allow blood to flow through the skirt via the slits 414.

In the illustrated embodiment of FIG. 25, the slits 414 are arranged in alternating axially extending columns 420a and 420b. The columns 420a can each comprise three slits and the columns 420b can each comprise two slits. In other embodiments, the slits 414 can be arranged on the outer skirt 400 in any pattern including any number of rows and/or columns containing any number of slits or any other pattern not having a particular number of rows and/or columns. Alternatively, the slits 414 can be arranged on the outer skirt 400 in a way that does not have a particular pattern. In some examples, the slits or openings 414 can have any of various other shapes, such as circular, square, rectangular, triangular, or various combinations thereof. In some examples, the slits or openings 414 can be elongated circumferentially or at any other angle with respect to the orientation of the outer skirt 400.

Referring to FIG. 26, the outer skirt 400 can be attached to the prosthetic heart valve 10 as previously described. As noted above, when the prosthetic valve 10 is implanted in a patient, the rough layer 202 of the pericardial tissue 200 can help to reduce and/or eliminate perivalvular leakage, as discussed above. Additionally, blood can flow through the slits 414, which can slow the flow of antegrade blood and further enhance blood clotting and tissue ingrowth, which can further help to prevent perivalvular leakage. Furthermore, the longitudinal or axial direction of the slits 414 can help reduce stretching or deformation of the outer skirt during passage through a sheath as may be caused by friction between the outer skirt and the inner surface of the sheath. Again, it should be noted that while outer skirt 400 is illustrated as being attached somewhat loosely, that is, with some slack in the intermediate portion 406 of the outer skirt 400, it can also be attached so as to fit more snugly against the outer surface of the frame 12.

FIGS. 27-29 show various ways of mounting an outer skirt (e.g., outer skirt 300 or outer skirt 400) to the frame 12 of a prosthetic valve 10. For purposes of illustration, reference number 400 is used to designate the outer skirt in FIGS. 27-29, although it should be understood that the other outer skirts disclosed herein can be mounted to the frame 12 in the same manner.

Referring to FIG. 27, the inner skirt 16 comprises an upper edge portion 48 and a lower edge portion 50. The upper edge portion 48 of the inner skirt 16 can be secured to the inside of the frame 12 such as via sutures 70 as previously described and as best shown in FIG. 21. Alternatively, the upper edge portion 48 of the inner skirt 16 can be secured to the inside of frame 12 via adhesive and/or ultrasonic welding in addition to or in lieu of sutures 70. The upper edge portion 402 of the outer skirt 400 can be secured to the frame 12 with sutures 468. The upper edge portions 48 and 402 are shown loosely attached to the frame in FIG. 27 for purposes of illustration, but typically are tightly secured to the frame struts as depicted in FIG. 1.

The lower edge portion 50 of the inner skirt 16 can be wrapped around the inflow end portion 15 of the frame 12 and around the lower edge portion 404 of the outer skirt 400. The lower edge portion 404 of the outer skirt 400 and the wrapped lower edge portion 50 of the inner skirt 16 can be secured together and/or secured to the frame 12, such as with sutures 470 and/or an adhesive. Wrapping the lower edge portion 50 of the inner skirt 16 around the lower edge portion 404 of the outer skirt 400 can reinforce the lower edge portion 404 and the sutures 470 along the lower edge portion 404. The lower edge portions 50 and 404 are shown loosely attached to the frame in FIG. 27 for purposes of illustration, but typically are tightly secured to the frame struts with the sutures 470.

FIGS. 28-29 show another way of mounting the outer skirt 400 to the frame 12. The upper edge portion 402 of the outer skirt 400 can be mounted to the frame 12 with sutures 468 as previously described herein. A reinforcing strip 448 having a first edge portion 450 and a second edge portion 452 can be wrapped around the inflow end portion 15 of the frame 12. The reinforcing strip 448 can be made of fabric material (e.g., PET) or natural tissue (e.g., pericardial tissue). In some embodiments, the reinforcing strip 448 can be used to secure the cusp portion of each leaflet 41 to the frame, as shown in FIG. 29.

Although not shown in FIGS. 28-29, in some embodiments, an inner skirt 16 also can be mounted inside of the frame 12. In some embodiments, the reinforcing strip 448 is part of an inner skirt that varies in height around the circumference of the inner skirt with a maximum height at the commissures of the leaflets (such as illustrated in FIG. 27) and a minimum height at a location equidistant between two commissures (such as illustrated in FIG. 28). Further details of a reinforcing strip that is used to attach the cusp portions of the leaflets to a frame and details of an inner skirt that has a maximum height at the commissures of the leaflets and a minimum height between the commissures are provided in U.S. Provisional Application No. 62/369,678, filed Aug. 1, 2016, which is incorporated herein by reference in its entirety.

The first edge portion 450 of the reinforcing strip 448 can be positioned inside of the frame 12 while the second edge portion 452 can be positioned outside the frame 12. The first and second edge portions 450, 452 can be attached to each other and/or to the frame 12, using sutures 470 and/or an adhesive. The edge portions 450, 452 are shown loosely attached to the frame in FIGS. 28-29 for purposes of illustration, but typically are tightly secured to the frame.

The second edge portion 452 of the reinforcing strip 448 can be wrapped around the lower edge portion 404 of the outer skirt 400 such that the lower edge portion 404 is between the frame 12 and the reinforcing strip 448. The lower edge portion 404 of the outer skirt 400 can be secured to the frame 12 and the second edge portion 452 of the reinforcing strip 448 with the sutures 470 and/or an adhesive. As depicted in FIG. 29, the lower cusp portion of each leaflet 41 can be secured between the frame 12 and the first edge portion 450 of the reinforcing strip 448 with sutures (e.g., with sutures 472) and/or an adhesive.

Referring to FIG. 29, the outer skirt 400 is shown protruding inwardly through the frame 12, which may occur during cycling and/or when the frame 12 is crimped to its radially collapsed configuration. When the outer skirt 400 protrudes through the frame 12, it may contact one of the leaflets 41. By having smooth surface 208 of the pericardial tissue facing inwards towards the frame 12, any contact between any of the leaflets 41 and the outer skirt 400 will be with the smooth surface 208 of the pericardial tissue 200 that forms the outer skirt 400, thereby preventing or minimizing abrasion of the leaflets 41.

Figure 30:
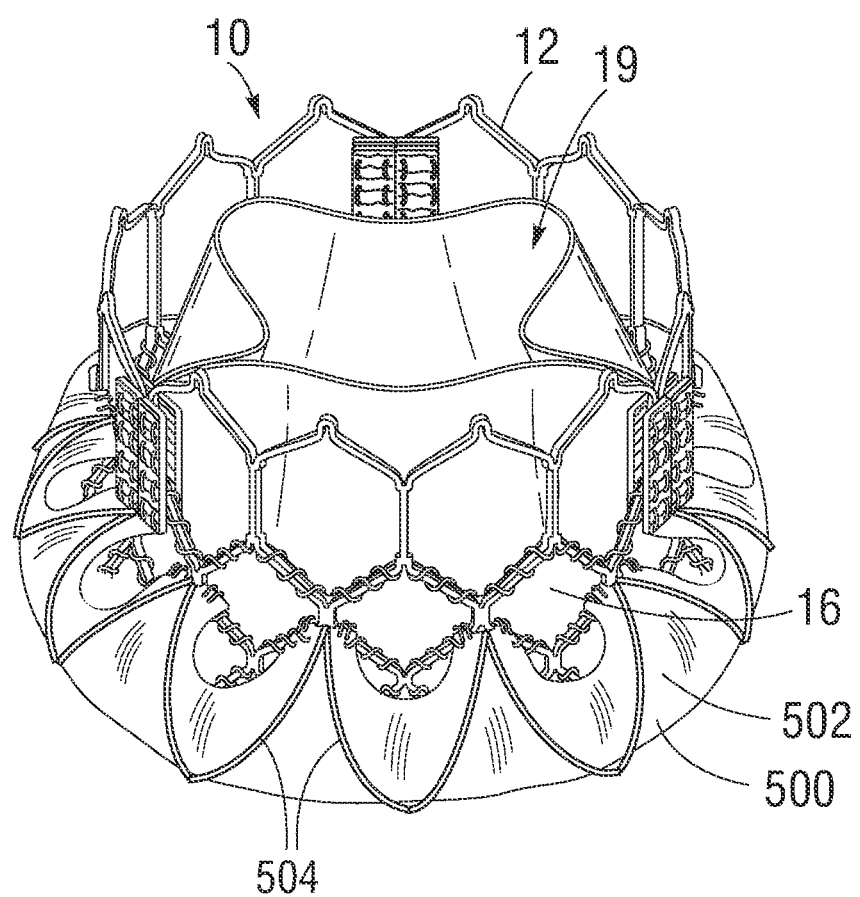
FIG. 30 shows another exemplary prosthetic heart valve.

FIG. 30 shows a prosthetic heart valve 10 having an outer skirt 500, according to another embodiment. The outer skirt 500 in the illustrated embodiment comprises a main body or layer 502 of pericardial tissue and a plurality of strips 504 of material mounted on the outer surface of the main body 502. The main body 502 can be the outer skirt 300 or the outer skirt 400. The strips 504 desirably are made from a substantially non-elastic and non-stretchable material. For example, the strips 504 can be sutures, pieces of woven fabric (e.g., PET strips), pieces of non-woven fabric, or other types of fibrous material. In the illustrated embodiment of FIG. 30, the strips 504 are arranged to form a repeating U-shaped pattern around the main body 502. Alternatively, the strips 504 can be arranged in any other pattern (e.g., the strips 504 can extend parallel to the longitudinal axis of the prosthetic valve). The strips 502 can facilitate passage of the prosthetic valve through an introducer sheath by reducing contact between the pericardial tissue forming the main body 502 and the inner surface of the sheath and by resisting stretching of the pericardial tissue caused by frictional contact with the inner surface of the sheath. Further, when formed from an absorbent material, such as fabric, the strips 504 can absorb blood to help enhance blood clotting and tissue ingrowth to further reduce perivalvular leakage. While outer skirt 500 is illustrated as being attached somewhat loosely, that is, with some slack in the main body 502 of the outer skirt 300, it can also be attached so as to fit more snugly against the outer surface of the frame 12.

The prosthetic valve 10 can be configured for and mounted on a suitable delivery apparatus for implantation in a subject. Several catheter-based delivery apparatuses can be used; a non-limiting example of a suitable catheter-based delivery apparatus includes that disclosed in U.S. Patent Application Publication No. 2013/0030519, which is incorporated by reference herein in its entirety, and U.S. Patent Application Publication No. 2012/0123529.

To implant a plastically-expandable prosthetic valve 10 within a patient, the prosthetic valve 10 including the outer skirt 400 (or alternatively, the outer skirt 300 or 500) can be crimped on an elongated shaft 180 of a delivery apparatus, as best shown in FIG. 13. The prosthetic valve, together with the delivery apparatus, can form a delivery assembly for implanting the prosthetic valve 10 in a patient's body. The shaft 180 comprises an inflatable balloon 182 for expanding the prosthetic valve within the body. With the balloon 182 deflated, the prosthetic valve 10 can then be percutaneously delivered to a desired implantation location (e.g., a native aortic valve region). Once the prosthetic valve 10 is delivered to the implantation site (e.g., the native aortic valve) inside the body, the prosthetic valve 10 can be radially expanded to its functional state by inflating the balloon 182.

Alternatively, a self-expanding prosthetic valve 10 can be crimped to a radially collapsed configuration and restrained in the collapsed configuration by inserting the prosthetic valve 10, including the outer skirt 400, into a sheath or equivalent mechanism of a delivery catheter. The prosthetic valve 10 can then be percutaneously delivered to a desired implantation location. Once inside the body, the prosthetic valve 10 can be advanced from the delivery sheath, which allows the prosthetic valve to expand to its functional state.

Figure 31:
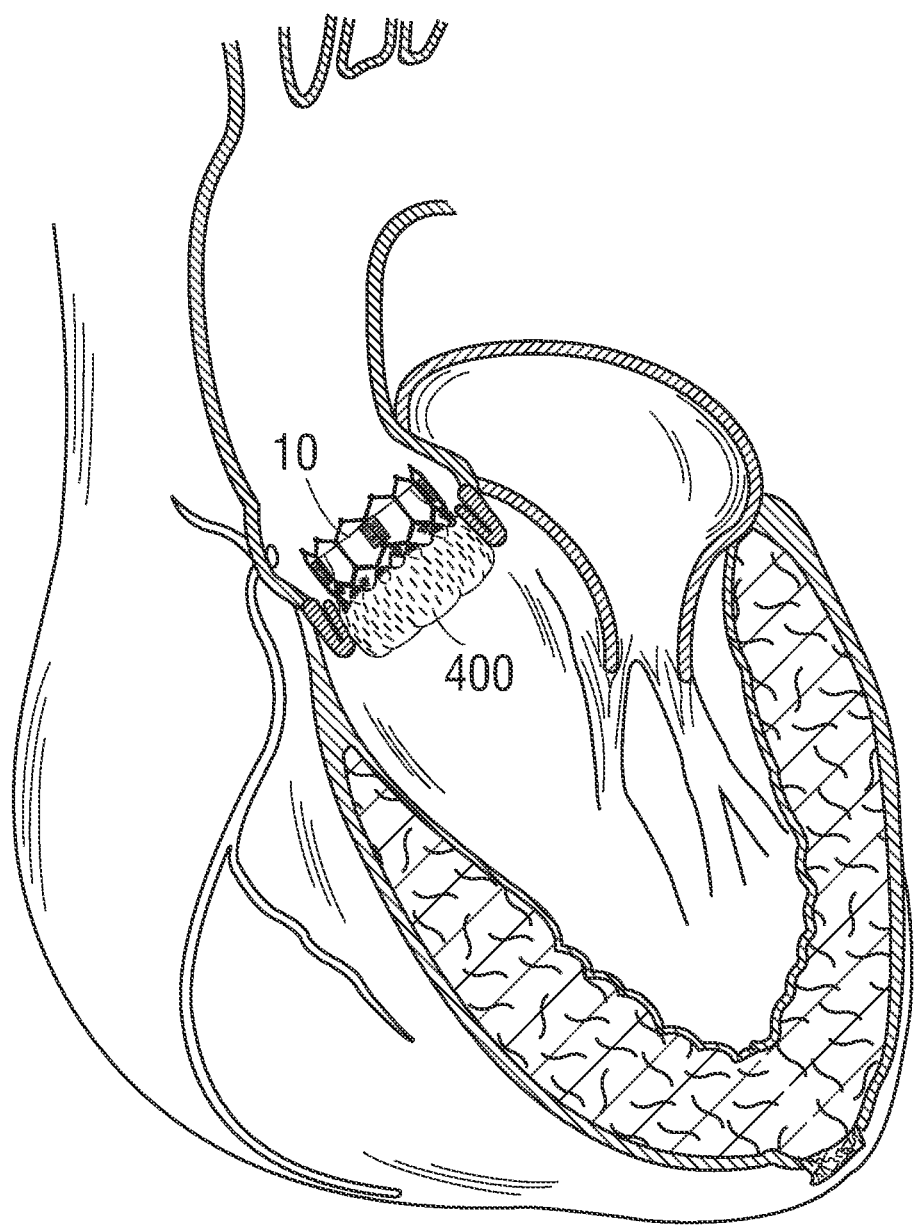
FIG. 31 shows an exemplary prosthetic heart valve implanted in the native aortic valve of a patient.

FIGS. 31-33 and 36 show various implantation positions for a prosthetic heart valve 10, including implantation within a dock or anchor placed inside the patient's body prior to valve implantation. FIG. 31 shows the prosthetic heart valve 10 implanted in the native aortic valve of a patient.

Figure 32:
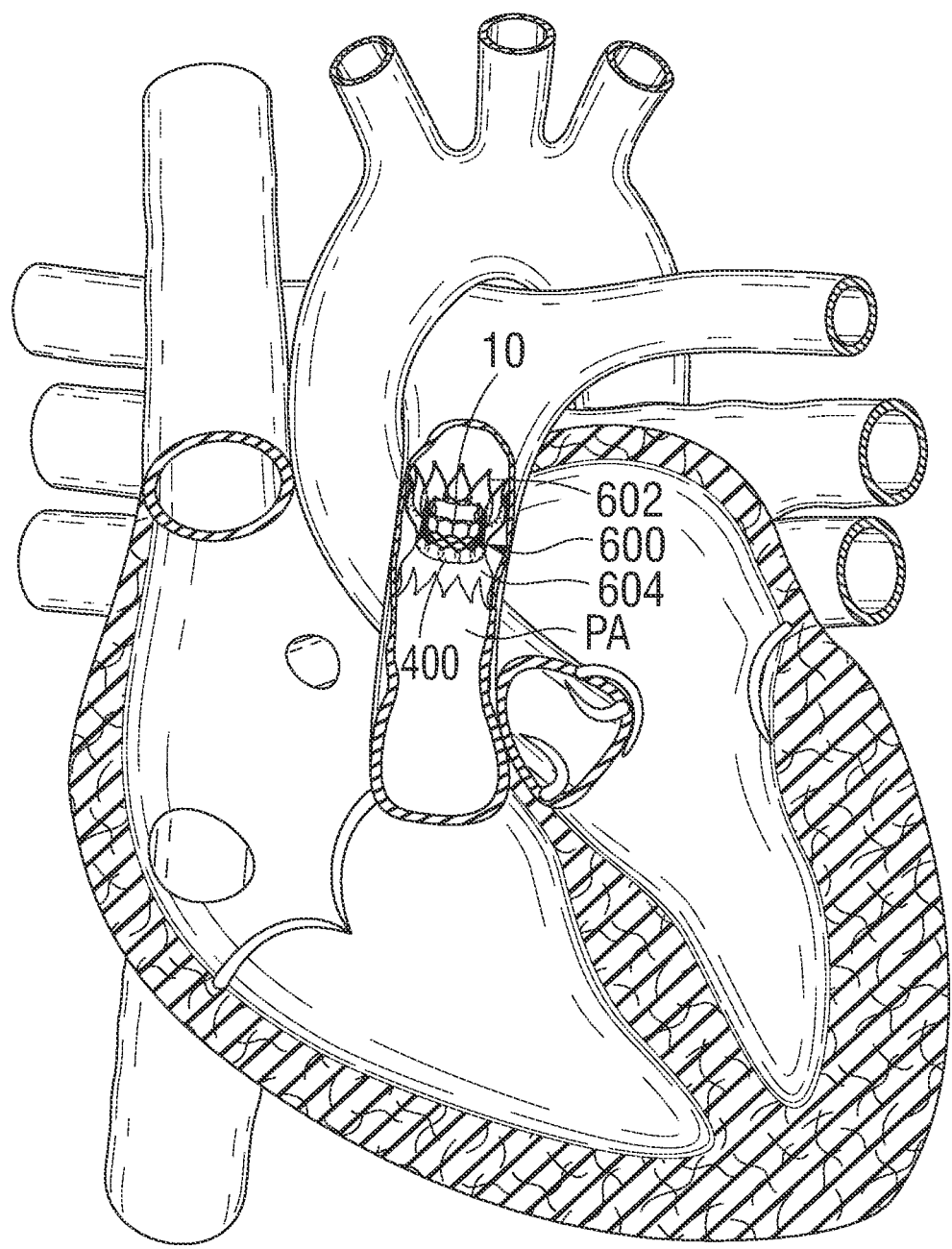
FIG. 32 shows an exemplary prosthetic heart valve and docking device implanted in the pulmonary artery of a patient.

FIG. 32 shows the prosthetic heart valve 10 implanted in the pulmonary artery of a patient for replacing or enhancing the function of a diseased pulmonary valve. Due to the variations in the size and shape of the native pulmonary valve and the pulmonary artery, the prosthetic valve 10 can be implanted within a radially expandable outer docking device 600. The docking device 600 can comprise a radially expandable and compressible annular stent 602 and a sealing member 604 that covers all or a portion of the stent and can extend across the inner surface and/or outer surface of the stent. The docking device 600 is configured to engage the inner wall of the pulmonary artery and can accommodate variations in patient anatomy. The docking device 600 also can compensate for the expanded prosthetic heart valve 10 being much smaller than vessel in which it is placed. The docking device 600 also can be used to support a prosthetic valve in other areas of the patient's anatomy, such as, the inferior vena cava, superior vena cava, or the aorta. Further details of the docking device 600 and methods for implanting the docking device and a prosthetic valve are disclosed, for example, in co-pending U.S. application Ser. No. 15/422,354, filed Feb. 1, 2017, which is incorporated herein by reference in its entirety.

Figure 33:
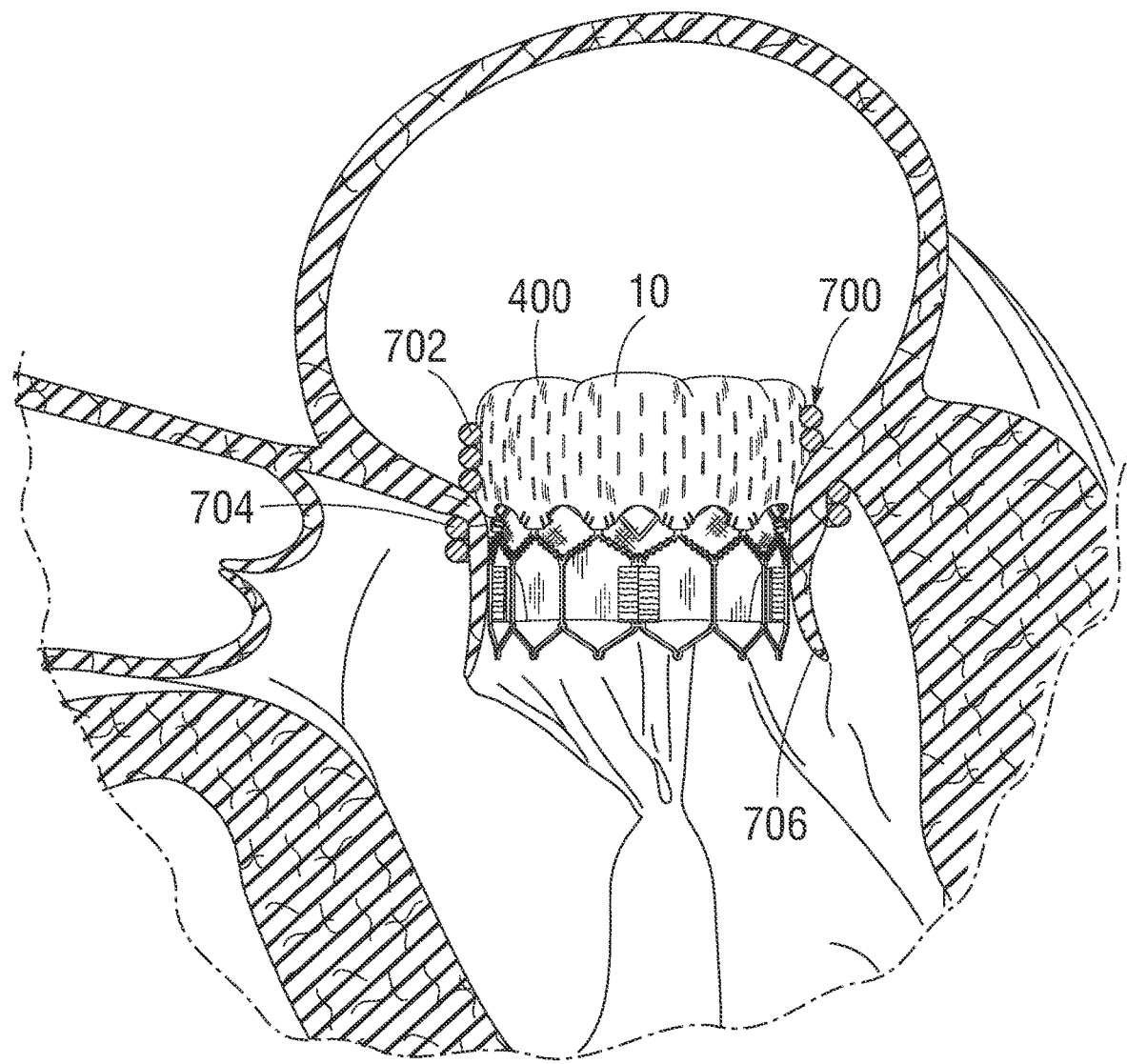
FIG. 33 shows an exemplary prosthetic heart valve and docking device implanted in the native mitral valve of a patient.

FIG. 33 shows the prosthetic heart valve 10 implanted in the native mitral valve of a patient using a docking device in the form of a helical anchor 700. The helical anchor 700 can include one or more coils 702 deployed in left atrium and one or more coils 704 deployed in the left ventricle and radially outside of the native mitral valve leaflets 706. When the prosthetic valve 10 is deployed within the native valve, the native leaflets are compressed or pinched between the prosthetic valve 10 and the anchor 700 to retain the prosthetic valve in place. Further details of the helical anchor 700 and methods for implanting the anchor and a prosthetic valve are disclosed, for example, in U.S. Application No. 62/395,940, filed Sep. 16, 2016, which is incorporated herein by reference in its entirety.

Figure 34:
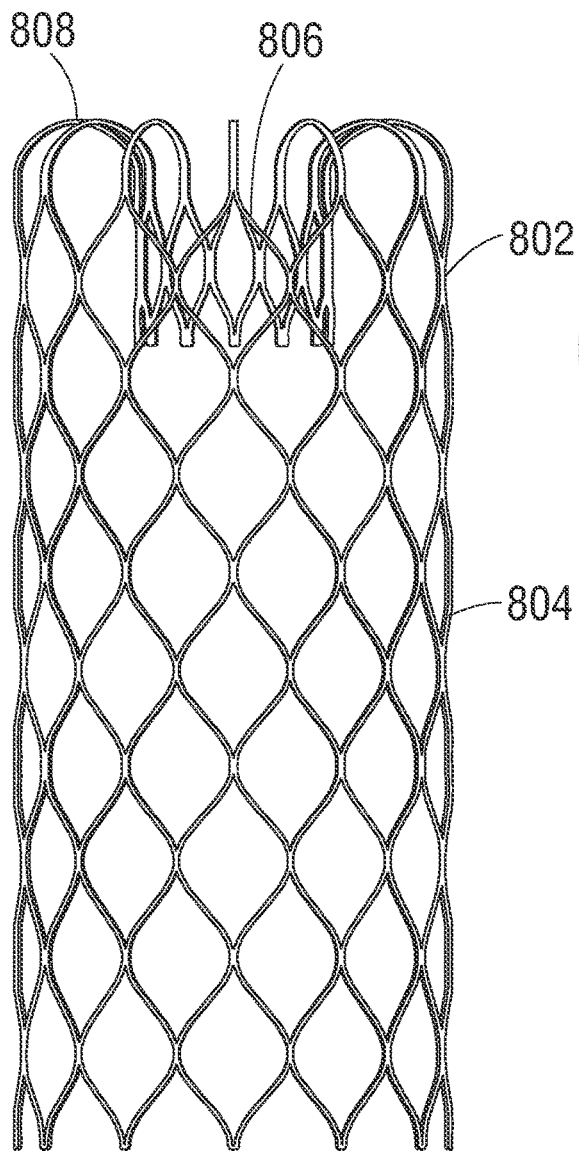
FIGS. 34-35 show an alternative embodiment of a docking device for a prosthetic valve.
Figure 35:
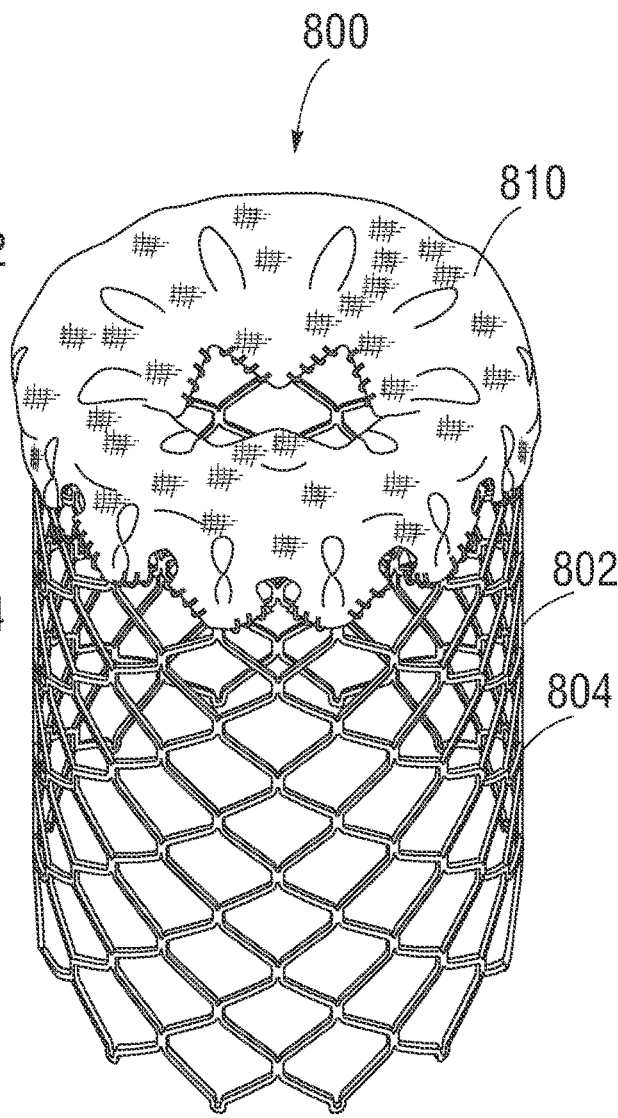

FIGS. 34 and 35 show a docking device 800 for a prosthetic heart valve, according to another embodiment. The docking device 800 can include a radially expandable and compressible frame 802 having an outer portion 804, an inner portion 806 disposed coaxially within one end portion of the outer portion 804, and a curved transition portion 808 extending between and connecting the inner portion 806 and the outer portion 804. The docking device 800 can further include a sealing member 810 extending over the inner surface of the inner portion 806, a portion of the outer surface of the outer portion 804 adjacent the inner portion 806, and the transition portion 808.

Figure 36:
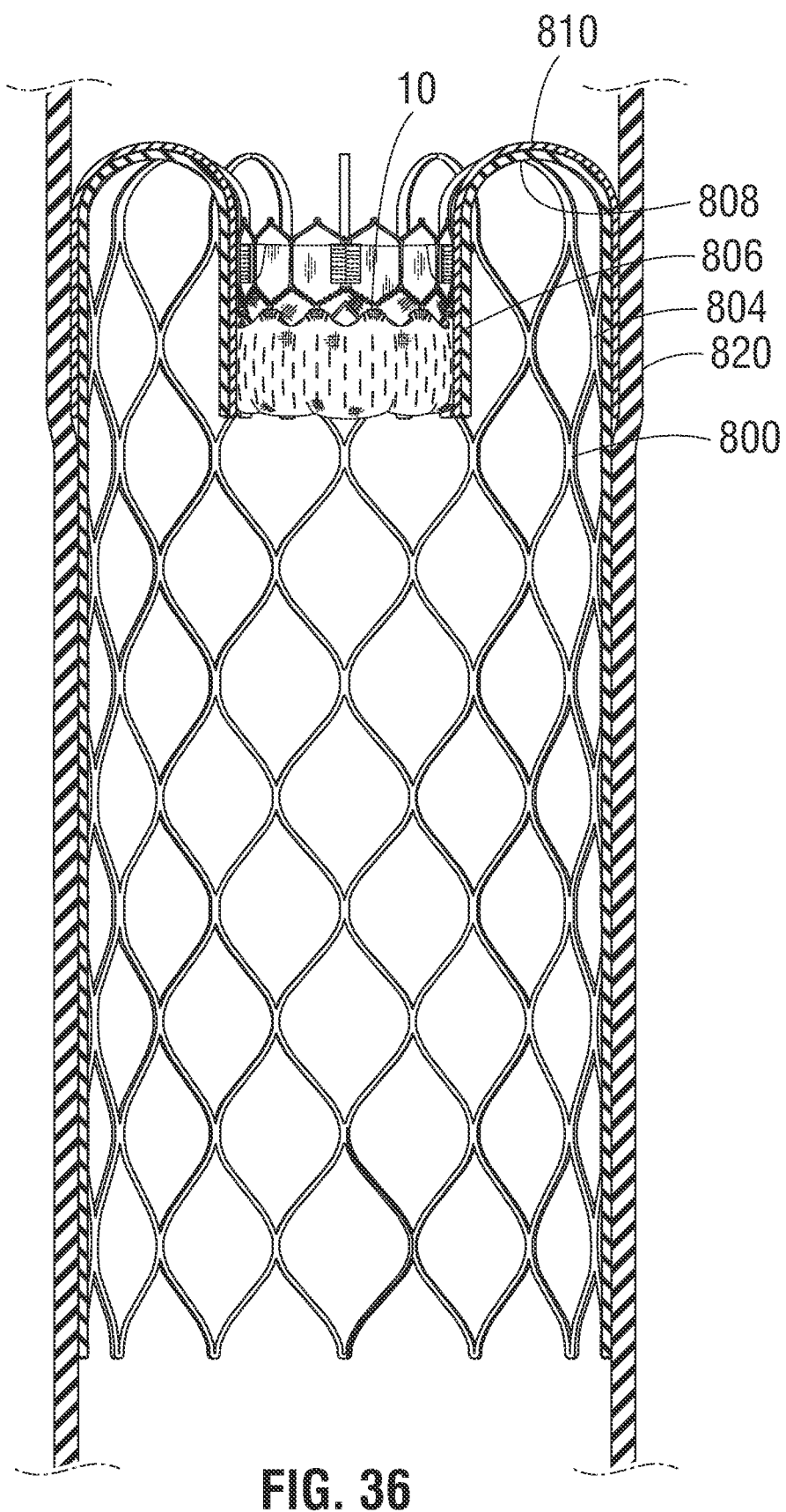
FIG. 36 shows an exemplary prosthetic heart valve and the docking device of FIGS. 34-35 implanted in the inferior vena cava of a patient.

FIG. 36 shows the docking device 800 implanted in a vessel 820, which can be, for example, the inferior vena cava, superior vena cava, or the ascending aorta. As shown, a prosthetic valve 10 can be deployed within the inner portion 806 of the docking device 800. Similar to the docking device 600, the docking device 800 can compensate for the expanded prosthetic heart valve 10 being much smaller than vessel in which it is placed. The docking device 800 is particularly suited for implanting a prosthetic valve in the inferior vena cava for replacing or enhancing the function of the native tricuspid valve. Further details of the docking device 800 and methods for implanting the docking device and a prosthetic valve are disclosed, for example, in co-pending U.S. application Ser. No. 16/034,794, filed Jul. 13, 2018, which is incorporated herein by reference.

General Considerations

It should be understood that the disclosed valves can be implanted in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed prostheses can also be implanted in other lumens of the body. Further, in addition to prosthetic valves, the delivery assembly embodiments described herein can be adapted to deliver and implant various other prosthetic devices such as stents and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. For example, an outer skirt for a prosthetic heart valve can include one or more features disclosed with respect to skirt 18, skirt 300, skirt 400, and/or skirt 500.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises." As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "coupled" and "associated" generally mean physically coupled or linked and does not exclude the presence of intermediate elements between the coupled or associated items absent specific contrary language.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as by the following claims.

The invention claimed is:

1. An implantable prosthetic valve comprising:
an annular frame comprising an inflow end and an outflow end and being radially collapsible and expandable between a radially collapsed configuration and a radially expanded configuration;
a leaflet structure positioned within the frame and secured thereto; and
an outer skirt positioned around an outer surface of the frame, wherein the outer skirt comprises pericardial tissue having a fibrous parietal layer defining a first surface of the outer skirt and a serous parietal layer defining a second surface of the outer skirt, the pericardial tissue having been fixed by cross-linking.

2. The prosthetic valve of claim 1, wherein the outer skirt comprises porcine pericardial tissue.

3. The prosthetic valve of claim 1, wherein the outer skirt has a thickness that is between 50 μm and 150 μm.

4. The prosthetic valve of claim 3, wherein the outer skirt has a thickness that is between 100 μm and 150 μm.

5. The prosthetic valve of claim 1, wherein the outer skirt comprises an outflow edge portion and an inflow edge portion, and wherein the outflow edge portion and the inflow edge portion are secured to the frame with sutures.

6. The prosthetic valve of claim 1, wherein the outer skirt comprises an outflow edge portion and an inflow edge portion, and wherein the outflow edge portion comprises a plurality of projections.

7. The prosthetic valve of claim 1, wherein the frame comprises a plurality of rows of angled struts arranged between the inflow end and the outflow end of the frame, including a first row of angled struts, a second row of angled struts, a third row of angled struts, a fourth row of angled struts, and a fifth row of angled struts, and wherein the first row of angled struts defines the inflow end of the frame.

8. The prosthetic valve of claim 7, wherein the outer skirt comprises an outflow edge portion and an inflow edge portion, and wherein the inflow edge portion is attached to the first row of angled struts and the outflow edge portion is attached to the third row of angled struts.

9. The prosthetic valve of claim 1, wherein the outer skirt extends between the inflow end of the frame and a portion of the frame disposed between the inflow end and the outflow end of the frame.

10. The prosthetic valve of claim 1, further comprising an inner skirt positioned around an inner surface of the frame and secured thereto.

11. The prosthetic valve of claim 10, wherein the inner skirt varies in height around a circumference of the inner skirt with a maximum height arranged in line with commissures of the leaflet structure and a minimum height arranged at a location equidistant between two commissures of the leaflet structure.

12. The prosthetic valve of claim 1, wherein the first surface is a relatively rough surface, as compared to the second surface, and wherein the second surface is a relatively smooth surface, as compared to the first surface.

13. An implantable prosthetic valve comprising:
an annular frame comprising an inflow end and an outflow end and being radially collapsible and expandable between a radially collapsed configuration and a radially expanded configuration;
a leaflet structure positioned within the frame and secured thereto; and
an outer skirt positioned around an outer surface of the frame, wherein the outer skirt comprises pericardial tissue with a relatively rough first surface and a relatively smooth second surface, the pericardial tissue having been fixed by cross-linking, wherein an inflow edge portion of the outer skirt is secured to the inflow end of the frame, and wherein an outflow edge portion of the outer skirt comprises a plurality of projections and is secured to a portion of the frame disposed between the inflow end and the outflow end of the frame.

14. The prosthetic valve of claim 13, wherein the inflow edge portion and the outflow edge portion of the outer skirt are secured to the frame with sutures.

15. The prosthetic valve of claim 13, wherein the outer skirt comprises porcine pericardial tissue.

16. The prosthetic valve of claim 13, further comprising an inner skirt positioned around an inner surface of the frame and secured thereto, wherein the inner skirt comprises pericardial tissue.

17. The prosthetic valve of claim 16, wherein an outflow edge portion of the inner skirt is formed with a plurality of projections that define an undulating shape.

18. An implantable prosthetic valve comprising:
an annular frame comprising an inflow end and an outflow end and being radially collapsible and expandable between a radially collapsed configuration and a radially expanded configuration;
a leaflet structure positioned within the frame and secured thereto;
an outer skirt positioned around an outer surface of the frame, wherein the outer skirt comprises pericardial tissue having a fibrous parietal layer and a serous parietal layer, the pericardial tissue having been fixed by cross-linking; and
an inner skirt positioned around an inner surface of the frame and secured thereto, wherein the inner skirt varies in height around a circumference of the inner skirt with a maximum height arranged in line with commissures of the leaflet structure and a minimum height arranged at a location equidistant between two commissures of the leaflet structure.

19. The prosthetic valve of claim 18, wherein the inner skirt comprises pericardial tissue.

20. The prosthetic valve of claim 18, wherein the fibrous parietal layer of the pericardial tissue of the outer skirt defines a first surface of the outer skirt, wherein the serous parietal layer defines a second surface of the outer skirt, and wherein the first surface is a relatively rough surface, as compared to the second surface, and the second surface is a relatively smooth surface, as compared to the first surface.

* * * * *